United States Patent
Ueda et al.

(10) Patent No.: US 9,295,656 B2
(45) Date of Patent: Mar. 29, 2016

(54) COMPOSITION CONTAINING REDUCED COENZYME Q10 AND PRODUCTION METHOD THEREOF

(75) Inventors: Takashi Ueda, Kakogawa (JP); Shinsuke Akao, Takasago (JP); Shiro Kitamura, Akashi (JP); Hideyuki Kishida, Kakogawa (JP); Takahiro Ueda, Kobe (JP)

(73) Assignee: KANEKA CORPORATION, Osaka (JP)

( * ) Notice: Subject to any disclaimer, the term of this patent is extended or adjusted under 35 U.S.C. 154(b) by 1066 days.

(21) Appl. No.: 11/812,887

(22) Filed: Jun. 22, 2007

(65) Prior Publication Data

US 2008/0026063 A1  Jan. 31, 2008

Related U.S. Application Data

(60) Provisional application No. 60/829,240, filed on Oct. 12, 2006.

(30) Foreign Application Priority Data

Jun. 22, 2006  (JP) .................................. 2006-172086
Apr. 24, 2007  (JP) .................................. 2007-114877

(51) Int. Cl.
    *A61K 31/122*  (2006.01)
    *A61K 9/00*    (2006.01)
    *A61K 9/16*    (2006.01)
    *A61K 9/20*    (2006.01)
    *A61K 9/48*    (2006.01)
    *A61K 9/107*   (2006.01)

(52) U.S. Cl.
    CPC .............. *A61K 31/122* (2013.01); *A61K 9/0056* (2013.01); *A61K 9/1652* (2013.01); *A61K 9/1664* (2013.01); *A61K 9/2018* (2013.01); *A61K 9/4858* (2013.01); *A61K 9/4875* (2013.01); *A61K 9/107* (2013.01)

(58) Field of Classification Search
    CPC .... A61K 31/122; A61K 9/0056; A61K 9/107
    See application file for complete search history.

(56) References Cited

U.S. PATENT DOCUMENTS

| | | | | |
|---|---|---|---|---|
| 5,989,583 | A * | 11/1999 | Amselem ...................... | 424/439 |
| 6,184,255 | B1 * | 2/2001 | Mae et al. ..................... | 514/720 |
| 6,740,338 | B1 | 5/2004 | Chopra | |
| 2003/0105168 | A1 | 6/2003 | Minemura et al. | |
| 2005/0147598 | A1 | 7/2005 | Ueda et al. | |
| 2006/0073131 | A1 | 4/2006 | Fujii et al. | |
| 2006/0204572 | A1 | 9/2006 | Higuchi et al. | |

FOREIGN PATENT DOCUMENTS

| | | |
|---|---|---|
| EP | 1 475 363 A1 | 11/2004 |
| EP | 1 681 053 A1 | 7/2006 |
| JP | 57-004916 | 1/1982 |
| JP | 62-198374 | 9/1987 |
| JP | 09-132775 | 5/1997 |
| JP | 2002-320453 | 11/2002 |
| JP | 2002-320454 | 11/2002 |
| WO | WO 01/52822 A1 | 7/2001 |
| WO | 2005/035477 A1 | 4/2005 |
| WO | WO 2005/041945 A1 | 5/2005 |
| WO | WO 2005/046696 A1 | 5/2005 |

OTHER PUBLICATIONS

Matthews et al. (Proc. Natl. Acad. Sci. 95, 8892-8897, 1998): Coenzyme Q10 administration increase . . . .*
Hsu et al. (Aaps Pharm. Sci. Tech. 4(3), 1-12, 2003) Preparation and characterization of . . . .*

* cited by examiner

*Primary Examiner* — Tigabu Kassa
(74) *Attorney, Agent, or Firm* — Sughrue Mion, PLLC

(57) ABSTRACT

The present invention provides a particulate composition wherein an oil component containing reduced coenzyme $Q_{10}$ is polydispersed forming a domain in a matrix containing a water-soluble excipient, which simultaneously shows high oxidative stability and high oral absorbability, a production method thereof, and a stabilizing method thereof. It also provides a food, food with nutrient function claims, food for specified health uses, dietary supplement, nutritional product, animal drug, drink, feed, pet food, cosmetic, pharmaceutical product, therapeutic drug, prophylactic drug and the like, which contain the composition.

20 Claims, 8 Drawing Sheets

AUC

AUC(μg/ml*hr)

| Comparative Example 1+fat and oil+surfactant | 6.12 |
| Example 5 | 4.99 |
| Example 8+ fat and oil+surfactant | 6.7 |
| Example 14 | 8.43 |
| Example 15 | 6.44 |
| Example 16 | 5.83 |

COMPOSITION CONTAINING REDUCED COENZYME Q10 AND PRODUCTION METHOD THEREOF

This application is a United States Application claiming benefit of Provisional Application 60/829240, filed on Oct. 12, 2006, which claims the benefit of JP 114877/2007, filed on Apr. 24, 2007 and JP 172086/2006, filed on Jun. 22, 2006, the contents of each of which are incorporated herein by reference.

TECHNICAL FIELD OF THE INVENTION

The present invention relates to a particulate composition containing reduced coenzyme $Q_{10}$ and a production method thereof. More particularly, the present invention relates to a particulate composition containing reduced coenzyme $Q_{10}$, which simultaneously shows high oxidative stability and high oral absorbability, and a production method thereof. In addition, the present invention relates to reduced coenzyme $Q_{10}$ in a noncrystalline state.

BACKGROUND OF THE INVENTION

Coenzyme Q is an essential component widely distributed in living organisms from bacteria to mammals. It is known that human coenzyme Q is mainly composed of coenzyme $Q_{10}$, having 10 repeat structures in its side chain. Coenzyme $Q_{10}$ is a physiological component present as a constituent component of the mitochondrial electron transport system in the cell of the living body. It functions as a transport component in the electron transport system by repeating oxidation and reduction in the living body.

Coenzyme $Q_{10}$ is known to show energy production, membrane stabilization and antioxidant activity in the living body, and has a high degree of usability. Coenzyme $Q_{10}$ occurs in two forms, the oxidized form and the reduced form, and it is known that, in the living body, usually about 40 to 90% of the coenzyme exists in the reduced form. Of coenzymes $Q_{10}$, oxidized coenzyme $Q_{10}$ (aka. ubiquinone or ubidecarenone) is widely used for pharmaceutical field as a drug for congestive heart failure. Besides the pharmaceutical use, it is widely used as an agent for oral preparation and a skin preparation, or as a nutritional product or a dietary supplement, like vitamin.

On the other hand, reduced coenzyme $Q_{10}$ shows higher oral absorbability than oxidized coenzyme $Q_{10}$, and is a superior compound effective as food, Food with nutrient function claims, Food for specified health uses, nutritional supplement, nutritional product, animal drug, drink, feed, pet food, cosmetic, pharmaceutical product, therapeutic drug, prophylactic drug and the like.

However, reduced coenzyme $Q_{10}$ is easily oxidized by molecular oxygen into oxidized coenzyme $Q_{10}$, and therefore, stabilization of reduced coenzyme $Q_{10}$ is an important issue when it is processed into a food, food with nutrient function claims, food for specified health use, nutritional supplement, nutritional product, animal drug, drink, feed, pet food, cosmetic, pharmaceutical product, therapeutic drug, prophylactic drug and the like, or a material or composition therefor, or during handling after processing and the like. Complete removal or blocking of oxygen during the above-mentioned handling is extremely difficult and remaining or admixed oxygen particularly during heating for processing and long-term preservation exerts a markedly adverse effect. The above-mentioned oxidation is directly related to quality problems such as the by-product oxidized coenzyme $Q_{10}$.

As mentioned above, stable retention (protection from oxidation) of reduced coenzyme $Q_{10}$ is an extremely important problem, for which little study has been done as to the method and composition for stably retaining reduced coenzyme $Q_{10}$. There are only a report on a composition concurrently containing a reducing agent and a production method thereof (WO01/052822) and a report on stabilization of reduced coenzyme $Q_{10}$ in fat and oil (WO03/062182).

WO01/052822 discloses methods for preparing 1) a composition comprising reduced coenzyme $Q_{10}$ and an amount of a reducing agent effective to prevent the oxidation of reduced coenzyme $Q_{10}$ to oxidized coenzyme $Q_{10}$; and an amount of a surfactant or a vegetable oil or a mixture thereof, and optionally, a solvent effective to solubilize the above-mentioned reduced coenzyme $Q_{10}$ and the aforementioned reducing agent,
2) a composition for oral administration obtained by formulating the above-mentioned composition into a gelatin capsule or tablet,
3) the above-mentioned composition containing reduced coenzyme $Q_{10}$ by the use of oxidized coenzyme $Q_{10}$ and a reducing agent in situ.

However, the above-mentioned WO01/052822 does not contain a detailed description relating to the quality, stabilizing effect and the like of reduced coenzyme $Q_{10}$ contained in the composition. In addition, the above-mentioned composition and preparation method thereof are highly complicated and troublesome because the composition plays multiple roles (i.e., role of reaction field for reducing oxidized coenzyme $Q_{10}$ to reduced coenzyme $Q_{10}$ and role of stably retaining reduced coenzyme $Q_{10}$). It is generally known that ascorbic acids (reducing agents) encapsulated in a gelatin capsule degrade disintegrability of the gelatin capsule, which in turn exerts an adverse influence on the absorbability in the living body.

Furthermore, it should be noted that since the above-mentioned composition and preparation method thereof use a reaction mixture as it is, the safety is not entirely secured. To be specific, ascorbic acids used as reducing agents for reducing oxidized coenzyme $Q_{10}$ to reduced coenzyme $Q_{10}$ are oxidized to give a considerable amount of dehydroascorbic acids, which remain in the above-mentioned compositions. The dehydroascorbic acids and oxalic acid produced by decomposition are highly harmful unlike ascorbic acids. For example, an increase in the lipoperoxide amount and a decrease in the antioxidant substance in the liver and kidney, as well as an increase in the amount of oxalic acid in the kidney have been reported, and side effects such as lower resistance to oxidative stress, easy onset of ureteral calculus and the like are feared.

In addition, WO03/062182 discloses, as a method for protecting reduced coenzyme $Q_{10}$ from oxidation, a stabilizing method of reduced coenzyme $Q_{10}$, comprising forming a composition containing reduced coenzyme $Q_{10}$, fats and oils (excluding olive oil) and/or polyol as a main component, which does not substantially inhibit stabilization of reduced coenzyme $Q_{10}$. However, the aforementioned stabilizing method may be insufficient to ensure stability of reduced coenzyme $Q_{10}$.

Moreover, the compositions described in WO01/052822 and WO03/062182 are oily compositions wherein reduced coenzyme $Q_{10}$ is dissolved in fats and oils and/or surfactant. Thus, the applicable ranges thereof are limited. Under the circumstances, there is a demand for a composition containing powdery and stable reduced coenzyme $Q_{10}$, which can be used for various applications.

DISCLOSURE OF THE INVENTION

Problems to be Solved by the Invention

To solve the aforementioned problems, the present invention proposes a particulate composition containing reduced coenzyme $Q_{10}$, which simultaneously shows high oxidative stability and high absorbability in the body, a production method thereof, and a stabilization method thereof, in the field of food, Food with nutrient function claims, Food for specified health uses, nutritional supplement, nutritional product, animal drug, drink, feed, pet food, cosmetic, pharmaceutical product, therapeutic drug, prophylactic drug and the like, a production method and a stabilizing method thereof. In addition, the present invention provides non-crystalline reduced coenzyme $Q_{10}$ and a reduced coenzyme $Q_{10}$ containing the non-crystalline reduced coenzyme $Q_{10}$, which are superior in the absorbability in the body.

Means of Solving the Problem

The present inventors have conducted intensive studies in an attempt to solve the aforementioned problems and found that a particulate composition wherein an oil component containing reduced coenzyme $Q_{10}$ is polydispersed forming a domain in a matrix containing a water-soluble excipient is a composition simultaneously having high oxidative stability and high oral absorbability, which resulted in the completion of the present invention.

[1] A particulate composition comprising an oil component (A) comprising reduced coenzyme $Q_{10}$ and a matrix comprising a water-soluble excipient wherein the oil component (A) is polydispersed forming a domain in the matrix.
[2] The particulate composition of [1], which has a sphericity of not less than 0.8.
[3] The particulate composition of [1] or [2], wherein not less than 10 wt % of the reduced coenzyme $Q_{10}$ in the particulate composition is non-crystalline.
[4] The particulate composition of any one of [1] to [3], wherein the oil component (A) is polydispersed forming not less than 5 domains.
[5] The particulate composition of any one of [1] to [4], wherein the water-soluble excipient is at least one kind selected from the group consisting of a water-soluble polymer, surfactant (C), sugar and a yeast cell wall.
[6.] The particulate composition of [5], wherein the water-soluble polymer is at least one kind selected from the group consisting of gum arabic, gelatin, agar, starch, pectin, carageenan, casein, dried albumen, curdlan, alginic acids, soybean polysaccharide, pullulan, celluloses, xanthan gum, carmellose salt and polyvinylpyrrolidone.
[7] The particulate composition of [5], wherein the surfactant (C) is at least one kind selected from the group consisting of glycerol fatty acid ester, sucrose fatty acid ester, sorbitan fatty acid ester, polyoxyethylenesorbitan fatty acid ester, lecithins and saponins.
[8] The particulate composition of [5], wherein the sugar is at least one kind selected from the group consisting of monosaccharide, disaccharide, oligosaccharide, sugar alcohol and polysaccharide.
[9] The particulate composition of any one of [1] to [8], wherein the oil component (A) containing reduced coenzyme $Q_{10}$ comprises 5-100 wt % of reduced coenzyme $Q_{10}$, 0-95 wt % of fat and oil, and 0-95 wt % of surfactant (D).
[10] The particulate composition of [9], wherein the surfactant (D) is at least one kind selected from the group consisting of glycerol fatty acid ester, polyglycerin ester, sucrose fatty acid ester, sorbitan fatty acid ester, propylene glycol fatty acid ester and polyoxyethylenesorbitan fatty acid ester, each having an HLB of not more than 10, and lecithins.
[11] The particulate composition of any one of [1] to [10], wherein the content of the reduced coenzyme $Q_{10}$ in the particulate composition is 1-70 wt %.
[12] The particulate composition of any one of [1] to [11], wherein the volume average particle size is 1-1000 μm.
[13] The particulate composition of any one of [1] to [12], wherein the domain formed by the oil component (A) has an average particle size of 0.01-50 μm.
[14] The particulate composition of any one of [1] to [13], which has a residual ratio of the reduced coenzyme $Q_{10}$ of not less than 50 wt % after preservation at 40° C. in the air in light shading for 30 days.
[15] A preparation comprising the particulate composition of any one of [1] to [14].
[16] A method of stabilizing a particulate composition or preparation comprising reduced coenzyme $Q_{10}$, which comprises placing the particulate composition of any one of [1] to [14], or the preparation of [15] in an environment of a surrounding relative humidity of not more than 90%.
[17] A method of handling a particulate composition or preparation comprising reduced coenzyme $Q_{10}$, which comprises placing the particulate composition of any one of [1] to [14], or the preparation of [15.] in an environment of a surrounding relative humidity of not more than 90%.
[18] A method of stabilizing a particulate composition or preparation comprising reduced coenzyme $Q_{10}$, which comprises wrapping or packaging the particulate composition of any one of [1] to [14] or the preparation of [15] with a glass, plastic and/or metal material.
[19] A method of handling a particulate composition or preparation comprising reduced coenzyme $Q_{10}$, which comprises wrapping or packaging the particulate composition of any one of [1] to [14] or the preparation of [15] with a glass, plastic and/or metal material.
[20] The stabilizing method of [16] or [18], which comprises concurrently using a moisture-proof agent.
[21] The handling method of [17] or [19], which comprises concurrently using a moisture-proof agent.
[22] A method of producing a particulate composition comprising reduced coenzyme $Q_{10}$, which comprises suspending a oil-in-water emulsion composition prepared from an oil component (A) containing reduced coenzyme $Q_{10}$ and an aqueous solution containing a water-soluble excipient in oil component (B), and removing water from the emulsion composition in oil component (B).
[23] The production method of [22], wherein the oil component (B) comprises 5-100 wt % of fat and oil and 0-95 wt % of surfactant (E).
[24] The production method of [22], wherein the oil component (B) comprises 5-99.99 wt % of fat and oil and 0.01-95 wt % of surfactant (E).
[25] The production method of [23] or [24], wherein the surfactant (E) is at least one kind selected from the group consisting of glycerol fatty acid ester, polyglycerin ester, sucrose fatty acid ester, sorbitan fatty acid ester and polyoxyethylenesorbitan fatty acid ester, each having an HLB of not more than 10, and lecithins.
[26] A method of producing a particulate composition comprising reduced coenzyme $Q_{10}$, which comprises spray drying, in a gaseous phase, an oil-in-water emulsion composition prepared from an oil component (A) comprising reduced coenzyme $Q_{10}$ and an aqueous solution comprising a water-soluble excipient.

[27] The production method of any one of [22] to [26], wherein the obtained particulate composition has a sphericity of not less than 0.8
[28] The production method of any one of [22] to [27], wherein the water-soluble excipient is at least one kind selected from the group consisting of a water-soluble polymer, surfactant (C), sugar and a yeast cell wall.
[29] The production method of [28], wherein the water-soluble polymer is at least one kind selected from the group consisting of gum arabic, gelatin, agar, starch, pectin, carageenan, casein, dried albumen, curdlan, alginic acids, soybean polysaccharide, pullulan, celluloses, xanthan gum, carmellose salt and polyvinylpyrrolidone.
[30] The production method of [28], wherein the surfactant (C) is at least one kind selected from the group consisting of glycerol fatty acid ester, sucrose fatty acid ester, sorbitan fatty acid ester, polyoxyethylenesorbitan fatty acid ester, lecithins and saponins.
[31] The production method of [28], wherein the sugar is at least one kind selected from the group consisting of monosaccharide, disaccharide, oligosaccharide, sugar alcohol and polysaccharide.
[32] The production method of any one of [22] to [31], wherein the oil component (A) comprising reduced coenzyme $Q_{10}$ comprises 5-100 wt % of reduced coenzyme $Q_{10}$, 0-95 wt % of fat and oil, and 0-95 wt % of surfactant (D).
[33] The production method of [32], wherein the surfactant (D) is at least one kind selected from the group consisting of glycerol fatty acid ester, polyglycerin ester, sucrose fatty acid ester, sorbitan fatty acid ester, propylene glycol fatty acid ester and polyoxyethylenesorbitan fatty acid ester, each having an HLB of not more than 10, and lecithins.
[34] The production method of any one of [22] to [33], wherein the obtained particulate composition has a residual ratio of not less than 50 wt % after preservation at 40° C. in the air in light shading for 30 days.
[35] A production method of a preparation comprising the step of any one of [22] to [34].
[36] A reduced coenzyme $Q_{10}$ which is not in a crystal state.
[37] A reduced coenzyme $Q_{10}$ wherein at least a part thereof is not crystal.
[38] A reduced coenzyme $Q_{10}$ wherein not less than 10 wt % is not crystal.

EFFECT OF THE INVENTION

The present invention provides a particulate composition containing reduced coenzyme $Q_{10}$, which is capable of maintaining high oral absorbability that reduced coenzyme $Q_{10}$ originally has and extremely stably retaining reduced coenzyme $Q_{10}$ unstable in the air. The present invention also provides an industrial production method of the particulate composition. In addition, the present invention also provides non-crystalline reduced coenzyme Q and reduced coenzyme $Q_{10}$ containing non-crystalline reduced coenzyme Q. Non-crystalline reduced coenzyme $Q_{10}$ is superior in absorbability in the body.

BEST MODE FOR EMBODYING THE INVENTION

Figure 1:
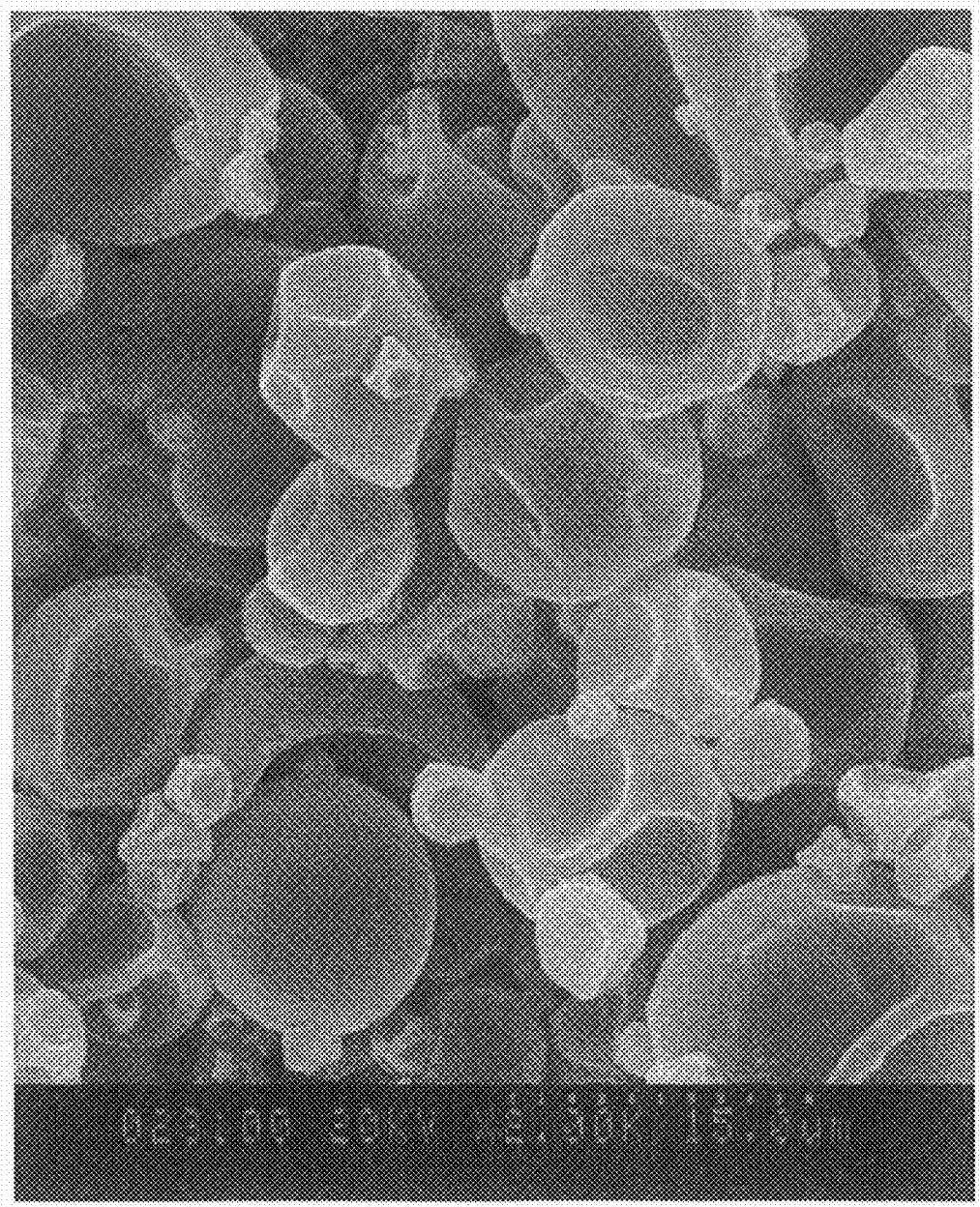
FIG. 1 shows an electron micrograph of the appearance of the particulate composition obtained in Example 1.

The particulate composition of the present invention is first explained. In the particulate composition of the present invention, an oil component (A) containing reduced coenzyme $Q_{10}$ is polydispersed forming a domain in a matrix containing a water-soluble excipient.

The reduced coenzyme $Q_{10}$ contained in the particulate composition of the present invention is represented by the following formula (1):

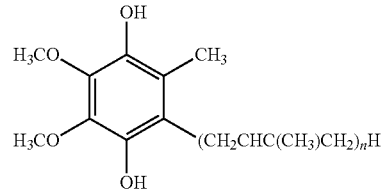

wherein n=10.

As mentioned above, coenzyme $Q_{10}$ occurs in a reduced form and an oxidized form. In the present invention, coenzyme $Q_{10}$ refers to reduced coenzyme $Q_{10}$. The particulate composition of the present invention essentially contains reduced coenzyme $Q_{10}$, which may be a reduced form alone or a mixture of oxidized coenzyme $Q_{10}$ and reduced coenzyme $Q_{10}$. When the particulate composition of the present invention contains both reduced coenzyme $Q_{10}$ and oxidized coenzyme $Q_{10}$, the proportion of reduced coenzyme $Q_{10}$ in the total amount of coenzyme $Q_{10}$ (i.e., total amount of reduced coenzyme $Q_{10}$ and oxidized coenzyme $Q_{10}$) is not particularly limited. For example, it is not less than about 20 wt %, generally not less than about 40 wt %, preferably not less than about 60 wt %, more preferably not less than about 80 wt %, particularly not less than about 90 wt %, and especially not less than about 96 wt %. While the upper limit is 100 wt % and is not particularly limited, it is generally not more than about 99.9 wt %.

Reduced coenzyme $Q_{10}$ can be produced, as described in JP-A-10-109933, for example, by a method comprising obtaining coenzyme $Q_{10}$ which is a mixture of oxidized coenzyme $Q_{10}$ and reduced coenzyme $Q_{10}$ by a conventionally known method such as synthesis, fermentation, extraction from a naturally occurring substance, and the like, concentrating reduced coenzyme $Q_{10}$ fraction in the eluent using chromatography and the like. In this case, oxidized coenzyme $Q_{10}$ contained in the above-mentioned coenzyme $Q_{10}$ may be reduced with a conventional reducing agent such as sodium borohydride, sodium dithionite (sodium dithionite) and the like, and concentrated by chromatography. In addition, reduced coenzyme $Q_{10}$ can be obtained by reacting existing high-purity oxidized coenzyme $Q_{10}$ with the above-mentioned reducing agent.

Preferably, it is obtained by reducing existing high-purity oxidized coenzyme $Q_{10}$, or coenzyme $Q_{10}$ which is a mixture of oxidized coenzyme $Q_{10}$ and reduced coenzyme $Q_{10}$, using a conventional reducing agent, for example, sodium hydrosulfite (sodium dithionite), sodium borohydride, ascorbic acids and the like. More preferably, it is obtained by reducing existing high-purity oxidized coenzyme $Q_{10}$, or coenzyme $Q_{10}$ which is a mixture of oxidized coenzyme $Q_{10}$ and reduced coenzyme $Q_{10}$, using ascorbic acids.

The matrix in the present invention retains an oil component (A) containing reduced coenzyme $Q_{10}$ and forms a particulate shape in the particulate composition. The matrix in the present invention contains a water-soluble excipient as a main component. The main component here means that not less than 80 wt % of the matrix component is a water-soluble excipient.

While the water-soluble excipient in the present invention is not particularly limited, it is preferably one kind selected from the group consisting of water-soluble polymer, surfactant (C), sugar, and yeast cell wall, or a mixture thereof. While the above-mentioned water-soluble excipient is not particularly limited as long as it is acceptable for food, cosmetic or pharmaceutical product, one acceptable for food is particularly preferable.

As the above-mentioned water-soluble polymer, for example, gum arabic, gelatin, agar, starch, pectin, carageenan, casein, casein compound, dried albumen, curdlan, alginic acids, soybean polysaccharides, pullulan, celluloses, xanthan gum, carmellose salt (carmellose sodium, carmellose calcium and the like), higher fatty acid sugar ester, tragacanth, water-soluble polymer containing amino acid and/or sugar and the like as main components such as milk and the like, polyvinylpyrrolidone and the like can be used singly or in a mixture of two or more kinds thereof. Of these, gum arabic, gelatin, agar, starch, pectin, carageenan, casein, dried albumen, curdlan, alginic acids, soybean polysaccharides, pullulan, celluloses, xanthan gum, carmellose salt and polyvinylpyrrolidone are preferable. Gum arabic, gelatin and soybean polysaccharides are more preferably used in view of the handlability of aqueous solution during production, or since a particulate composition simultaneously having high oxidative stability and high absorbability in the living body, which is the object of the present invention, can be obtained.

While the above-mentioned surfactant (C) is not particularly limited as long as it is acceptable for food, cosmetic and pharmaceutical product, one particularly acceptable for food is preferable. For example, glycerol fatty acid esters, sucrose fatty acid esters, sorbitan fatty acid esters, polyoxyethylenesorbitan fatty acid ester, lecithins and saponins can be used. It is needless to say that they can be used alone or in a mixture of two or more kinds thereof in the present invention.

As the aforementioned glycerol fatty acid esters, for example, fatty acid and organic acid esters of monoglycerol, polyglycerol fatty acid esters, polyglycerin condensed ricinoleate and the like can be mentioned.

As the fatty acid and organic acid esters of monoglycerol, for example, stearic acid and citric acid ester of monoglycerol, stearic acid and acetic acid ester of monoglycerol, stearic acid and succinic acid ester of monoglycerol, caprylic acid and succinic acid ester of monoglycerol, stearic acid and lactic acid ester of monoglycerol, stearic acid and diacetyltartaric acid ester of monoglycerol and the like can be mentioned.

As the polyglycerol fatty acid ester, for example, one having an average degree of polymerization of polyglycerin of 2-10, wherein the constituent fatty acid has 6 to 22 carbon atoms, can be mentioned.

As the aforementioned polyglycerin condensed ricinoleate, for example, one having an average degree of polymerization of polyglycerin of 2-10, wherein the average degree of condensation of polyricinoleic acid (average number of condensation of ricinoleic acid) is 2 to 4, can be mentioned.

As the aforementioned sucrose fatty acid esters, one wherein one or more hydroxyl groups of sucrose is/are each esterified with fatty acid having 6 to 18, preferably 6 to 12, carbon atoms can be mentioned.

As the aforementioned sorbitan fatty acid esters, one wherein one or more hydroxyl groups of sorbitan is/are each esterified with fatty acid having 6 to 18, preferably 6 to 12, carbon atoms can be mentioned.

As the aforementioned polyoxyethylenesorbitan fatty acid esters, one wherein one or more hydroxyl groups of sorbitan has/have a polyoxyethylene chain and one or more hydroxyl groups is/are esterified with fatty acid having 6 to 18, preferably 6 to 12, carbon atoms can be mentioned.

As the aforementioned lecithins, for example, egg-yolk lecithin, purified soybean lecithin, phosphatidylcholine, phosphatidylethanolamine, phosphatidylserine, sphingomyelin, dicetyl phosphate, stearylamine, phosphatidylglycerol, phosphatidic acid, phosphatidylinositolamine, cardiolipin, ceramide phosphorylethanolamine, ceramide phosphoryl glycerol, enzymatically decomposed lecithin (lysolecithin) and a mixture thereof and the like can be mentioned.

As the aforementioned saponins, for example, enju saponin, quillaja saponin, soybean saponin, yucca saponin and the like can be mentioned.

Of the above-mentioned surfactant (C), surfactant (C) is preferably a hydrophilic surfactant and, for example, a surfactant having an HLB of not less than 4, generally not less than 6, preferably not less than 8, more preferably not less than 9.5, more preferably not less than 11 can be used because an oil component containing reduced coenzyme $Q_{10}$ can be emulsified stably, and a particulate composition simultaneously having high oxidative stability and high absorbability in the living body, which is the object of the present invention, can be obtained.

As such surfactant, specifically, fatty acid and organic acid esters of monoglycerol such as stearic acid and citric acid ester of monoglycerol, stearic acid and diacetyltartaric acid ester of monoglycerol and the like; polyglycerol fatty acid esters such as triglycerol monolaurate, triglycerol monomyristate, triglycerol monooleate, triglycerol monostearate, pentaglycerol monomyristate, pentaglycerol trimyristic acid ester, pentaglycerol monooleate, pentaglycerol trioleate, pentaglycerol monostearate, pentaglycerol tristearate, hexaglycerol monocaprylate, hexaglycerol dicaprylate, hexaglycerol monolaurate, hexaglycerol monomyristate, hexaglycerol monooleate, hexaglycerol monostearate, decaglycerol monolaurate, decaglycerol monomyristate, decaglycerol monooleate, decaglycerol monopalmitic acid ester, decaglycerol monostearate, decaglycerol distearate and the like; polyglycerin condensed ricinoleate such as tetraglycerol condensed ricinoleate, pentaglycerol condensed ricinoleate, hexaglycerol condensed ricinoleate, diglycerol condensed ricinoleate and the like; sorbitan fatty acid esters such as sorbitan monostearate, sorbitan monooleate and the like; polyoxyethylenesorbitan fatty acid ester such as polyoxyethylenesorbitan monostearate, polyoxyethylenesorbitan monooleate and the like, sucrose fatty acid esters such as sucrose palmitate, sucrose stearate and the like; lecithins such as soybean lecithin, egg-yolk lecithin, enzymatically decomposed lecithin and the like; and saponins such as enju saponin, quillaja saponin, soybean saponin, yucca saponin and the like can be mentioned.

The above-mentioned sugar is not particularly limited as long as it is acceptable for food and, for example, monosaccharides such as glucose, fructose, galactose, arabinose, xylose, mannose and the like; disaccharides such as maltose, sucrose, lactose and the like; oligosaccharides such as fructooligosaccharide, soybean oligosaccharide, galactooligosaccharide, xylo-oligosaccharide and the like; sugar alcohols such as sorbitol, maltitol, erythritol, lactitol, xylitol and the like; polysaccharides such as dextrin and the like; and the like can be preferably used.

The dextrin is not particularly limited, and a degradation product of starch can be used, where both low molecular weight dextrin and high molecular weight dextrin can be preferably used. However, from the aspect of solubility in aqueous layer and the like, dextrin having a dextrose equivalent (DE) of generally not more than 40, preferably not more than 35, more preferably not more than 30, and generally not less than 1, preferably not less than 2, more preferably not less than 5, can be preferably used. Moreover, dextrin may be maltodextrin, cyclodextrin, cluster dextrin and the like.

As the above-mentioned yeast cell wall, beer yeast cell wall and the like can be mentioned.

In the present invention, water-soluble polymer and sugar are preferably used in combination as the water-soluble excipient. It is more preferable to combine gum arabic as the water-soluble polymer and sucrose or dextrin as the sugar. When a water-soluble polymer and sugar are used in combination, the weight ratio of water-soluble polymer and sugar is not particularly limited. The weight of the water-soluble polymer relative to the total weight of water-soluble polymer and sugar is generally not less than 25%, preferably not less than 40%, more preferably not less than 50%, particularly preferably not less than 60%, and generally not more than 99%, preferably not more than 95%, more preferably not more than 90%, particularly preferably not more than 85%.

The oil component (A) containing reduced coenzyme $Q_{10}$ in the particulate composition of the present invention may be (1) reduced coenzyme $Q_{10}$ alone, or coenzyme $Q_{10}$ which is a mixture of reduced coenzyme $Q_{10}$ and oxidized coenzyme $Q_{10}$ (hereinafter to be simply referred to as coenzyme $Q_{10}$) alone, or (2) a mixture of reduced coenzyme $Q_{10}$ or coenzyme $Q_{10}$, and fat and oil and/or a surfactant (D). When the oil component (A) is a mixture of reduced coenzyme $Q_{10}$ or coenzyme $Q_{10}$, and fat and oil and/or a surfactant (D), it is preferably an oil component that is visually uniformly mixed when heat-melted at 50° C. or above. From the aspect of maintaining a high content of reduced coenzyme $Q_{10}$ in oil component (A), the above-mentioned (1) is preferable.

The fats and oils to be used when oil component (A) is the aforementioned (2) are not particularly limited and, for example, may be natural fats and oils from plants and animals, synthetic fats and oils or processed fats and oils. More preferably, one acceptable for food, cosmetic or pharmaceutical agent is used. Examples of vegetable oil include coconut oil, palm oil, palm kernel oil, flaxseed oil, camellia oil, brown rice germ oil, canola oil, rice oil, peanuts oil, corn oil, wheat germ oil, soy bean oil, perilla oil, cottonseed oil, sunflower kerel oil, kapok oil, evening primrose oil, shea butter, sal butter, cacao butter, sesame oil, safflower oil, olive oil and the like, and examples of animal fats and oils include lard, milk fat, fish oil, beef fat and the like. Furthermore, fats and oils obtained by processing them such as by fractionation, hydrogenation, transesterification (e.g., hydrogenated oil) and the like are also included. It is needless to say that medium-chain triglyceride (MCT) and the like can also be used. A mixture thereof may be used. As the medium chain triglyceride, for example, triglyceride wherein fatty acid has 6 to 12, preferably 8 to 12, carbon atoms can be mentioned.

Of the above-mentioned fats and oils, vegetable fats and oils, synthetic fats and oils and processed fats and oils are preferable from the aspects of handlability, odor and the like. For example, coconut oil, palm oil, palm kernel oil, canola oil, rice oil, soy bean oil, cottonseed oil, safflower oil, olive oil, MCT and the like can be mentioned.

As the surfactant (D) to be used when oil component (A) is the aforementioned (2), for example, glycerol fatty acid esters, polyglycerin esters, sucrose fatty acid esters, sorbitan fatty acid esters, propylene glycol fatty acid esters or polyoxyethylenesorbitan fatty acid ester, a surfactant having an HLB of not more than 10 or lecithins and the like are preferable, but the surfactant is not limited to these.

As such glycerol fatty acid esters, for example, monoglycerides and diglycerides wherein fatty acid has 6 to 18, preferably 6 to 12, carbon atoms can be mentioned. As the polyglycerin esters, for example, polyglycerin comprising polyglycerin having a polymerization degree of 2 to 10 as a main component, wherein one or more hydroxyl groups of polyglycerin is/are esterified with fatty acid having 6 to 18, preferably 6 to 12, carbon atoms can be mentioned. As the sucrose fatty acid esters, one wherein one or more hydroxyl groups of sucrose is/are esterified with fatty acid having 6 to 18, preferably 6 to 12, carbon atoms can be mentioned. As the sorbitan fatty acid esters, one wherein one or more hydroxyl groups of sorbitan is/are esterified with fatty acid having 6 to 18, preferably 6 to 12, carbon atoms can be mentioned. As the propylene glycol fatty acid esters, for example, monoglycerides and diglycerides wherein fatty acid has 6 to 18, preferably 6 to 12, carbon atoms can be mentioned. As the polyoxyethylenesorbitan fatty acid esters, one wherein one or more hydroxyl groups of sorbitan has/have a polyoxyethylene chain and one or more hydroxyl groups is/are esterified with fatty acid having 6 to 18, preferably 6 to 12, carbon atoms can be mentioned. As the lecithins, for example, egg-yolk lecithin, purified soybean lecithin, phosphatidylcholine, phosphatidylethanolamine, phosphatidylserine, sphingomyelin, dicetyl phosphate, stearylamine, phosphatidylglycerol, phosphatidic acid, phosphatidylinositolamine, cardiolipin, ceramide phosphorylethanolamine, ceramide phosphoryl glycerol, enzymatically decomposed lecithin (lysolecithin), and a mixture thereof and the like can be mentioned.

Of the above-mentioned surfactant (D), a hydrophilic surfactant is preferable and, for example, a surfactant having an HLB of not more than 9, preferably not more than 8, more preferably not more than 6, still more preferably less than 5 can be used because it shows good compatibility with reduced coenzyme $Q_{10}$, and a particulate composition simultaneously having high oxidative stability and high absorbability in the living body, which is the object of the present invention, can be obtained. Lecithins can be preferably used without limitation by its HLB.

As such surfactant, specifically, monoglycerol monofatty acid esters such as monoglycerol monostearate, monoglycerol monooleate, monoglycerol monomyristate, monoglycerol monocaprylate, monoglycerol monolaurate, monoglycerol monobehenate, monoglycerol monoerucate and the like; monoglycerol difatty acid esters such as monoglycerol distearate, monoglycerol dioleate, monoglycerol dicaprylate, monoglycerol dilaurate and the like; fatty acid and organic acid esters of monoglycerol such as stearic acid and citric acid ester of monoglycerol, stearic acid and acetic acid ester of monoglycerol, hydrogenated coconut oil and acetic acid ester of monoglycerol, stearic acid and succinic acid ester of monoglycerol, caprylic acid and succinic acid ester of monoglycerol, stearic acid and lactic acid ester of monoglycerol, stearic acid and diacetyltartaric acid ester of monoglycerol and the like; monoglycerol fatty acid esters obtained using various fats and oils such as hydrogenated beef tallow and fatty acid esters of monoglycerol, hydrogenated canola oil and fatty acid esters of monoglycerol, hydrogenated soybean oil and fatty acid esters of monoglycerol, cottonseed oil and fatty acid esters of monoglycerol, safflower oil and fatty acid esters of monoglycerol and the like; polyglycerol fatty acid esters such as ester of polyglycerin having an average polymerization degree of 2-10 and fatty acid having 6 to 22 carbon atoms and the like; propylene glycol fatty acid esters such as propylene glycol monostearate, propylene glycol monooleate, and propylene glycol monolaurate and the like; sorbitan fatty acid esters such as sorbitan distearate, sorbitan tristearate, sorbitan sesquioleate, sorbitan dioleate, and sorbitan trioleate and the like; polyoxyethylenesorbitan fatty acid ester such as polyoxyethylenesorbitan monostearate, polyoxyethylenesorbitan monooleate and the like, and a mixture of one or more kinds selected from lecithins such as soybean lecithin, egg-yolk lecithin, enzymatically decomposed lecithin and the like can be mentioned. Of these, preferred is a mixture of one or more kinds selected from glycerol fatty acid esters and lecithins, more preferred is a mixture of one or more kinds selected from monoglycerol monofatty acid esters, monoglycerol difatty acid esters, fatty acid and organic acid esters of monoglycerol (particularly fatty acid and acetic acid esters of monoglycerol, hydrogenated coconut oil and acetic acid ester of monoglycerol), polyglycerol fatty acid esters (particularly diglycerol monofatty acid esters) and polyglycerin condensed ricinoleate (particularly ester of polyglycerin having an average degree of polymerization of 2-10 and polyricinoleic acid having a condensation degree of 2-4), soybean lecithin, egg-yolk lecithin, and enzymatically decomposed lecithin, more preferred are fatty acid and organic acid esters of monoglycerol (particularly fatty acid and acetic acid esters of monoglycerol, hydrogenated coconut oil and acetic acid esters of monoglycerol), diglycerol monooleate, soybean lecithin, egg-yolk lecithin and enzymatically decomposed lecithin. Specific examples of the above-mentioned fatty acid and acetic acid esters of monoglycerol, hydrogenated coconut oil and acetic acid esters of monoglycerol include 50% acetylated product of monoglycerol monostearate, completely acetylated product of hydrogenated coconut oil monoglyceride.

Besides the above-mentioned, the oil component (A) in the present invention may contain, according to various objects, an oil-soluble component such as solid fat and oil, fatty acid and ester derivatives thereof and the like.

As the aforementioned solid fat and oil, for example, wax for food such as bees wax, vegetable wax, candelilla wax, rice bran wax, carnauba wax, snow wax and the like can be mentioned.

The aforementioned fatty acid and ester derivatives thereof include, but are not limited to, caprylic acid, capric acid, lauric acid, myristic acid, palmitic acid, stearic acid, oleic acid, behenic acid and esters thereof, for example, methyl ester, ethyl ester and the like thereof.

While the composition ratio of an oil component (A) containing reduced coenzyme $Q_{10}$ in the particulate composition of the present invention is not particularly limited, the content of reduced coenzyme $Q_{10}$ in oil component (A) is generally not less than 5 wt %, preferably not less than 20 wt %, more preferably not less than 40 wt %, more preferably not less than 50 wt %, particularly preferably not less than 60 wt %, from the aspect of prevention of a decrease in the content of reduced coenzyme $Q_{10}$ in the finally obtained particulate composition containing reduced coenzyme $Q_{10}$. The upper limit of the content of reduced coenzyme $Q_{10}$ in oil component (A) is of course 100 wt %, and use of fats and oils and surfactant other than reduced coenzyme $Q_{10}$ as oil component (A) is not always necessary. However, when fat and oil or surfactant is used, the upper limit of the content of reduced coenzyme $Q_{10}$ in oil component (A) is 99.99 wt %. The content of fat and oil in oil component (A) is generally not more than 95 wt %, preferably not more than 75 wt %, more preferably not more than 50 wt %, particularly preferably not more than 30 wt %. Use of fats and oils is not always necessary and the lower limit thereof is 0 wt % and generally not less than 0.01 wt % when it is to be used. The content of the surfactant is generally not more than 95 wt %, preferably not more than 75 wt %, more preferably not more than 50 wt %, particularly preferably not more than 30 wt %. Use of surfactant is not always necessary and the lower limit thereof is 0 wt % and generally not less than 0.01 wt % when it is to be used. That is, as the composition, oil component (A) preferably contains 5-100 wt % of reduced coenzyme $Q_{10}$, 0-95 wt % of fat and oil, 0-95 wt % of surfactant, more preferably contains 20-100 wt % of reduced coenzyme $Q_{10}$, 0-75 wt % of fat and oil, and 0-75 wt % of surfactant, more preferably contains 40-100 wt % of reduced coenzyme $Q_{10}$, 0-50 wt % of fat and oil, and 0-50 wt % of surfactant, particularly preferably contains 50-100 wt % of reduced coenzyme $Q_{10}$, 0-50 wt % of fat and oil, and 0-50 wt % of surfactant, and particularly preferably contains 60-100 wt % of reduced coenzyme $Q_{10}$, 0-50 wt % of fat and oil, and 0-50 wt % of surfactant. It is needless to say that the reduced coenzyme $Q_{10}$ here may be a mixture of reduced coenzyme $Q_{10}$ and oxidized coenzyme $Q_{10}$, i.e., coenzyme $Q_{10}$.

The average particle size of the domain formed by the oil component (A) containing reduced coenzyme $Q_{10}$ in the particulate composition of the present invention is not particularly limited as long as the object of the present invention can be achieved. When the average particle size of the domain formed is large, absorbability of the particulate composition may decrease. Thus, the average particle size is generally not more than 50 μm, preferably not more than 20 μm, more preferably not more than 15 μm, particularly preferably not more than 10 μm. On the other hand, when the average particle size of the domain is small, problems occur in that excess water-soluble excipient is needed to maintain stability of emulsion droplet during the production process, excess load is applied to an emulsification apparatus and the like. Thus, the average particle size is generally 0.001 μm, preferably not less than 0.005 μm, more preferably not less than 0.01 μm, particularly preferably not less than 0.1 μm.

The average particle size of the domain formed by an oil component (A) containing reduced coenzyme $Q_{10}$ can be determined by rupturing a particulate composition into hemisphere, followed by image analysis of electron microscopic images of the broken-out section thereof.

While the content of reduced coenzyme $Q_{10}$ in the particulate composition of the present invention is not particularly limited, it is generally not less than 1 wt %, preferably not less than 5 wt %, more preferably not less than 10 wt %, from the aspect of reducing the amount of ingestion of the particulate composition necessary for intake of a given amount of reduced coenzyme $Q_{10}$. On the other hand, it is generally not more than 70 wt %, preferably not more than 50 wt %, more preferably not more than 40 wt %, from the aspect of maintaining the high stability of reduced coenzyme $Q_{10}$ in the particulate composition. That is, the content of reduced coenzyme $Q_{10}$ in the particulate composition of the present invention is generally 1-70 wt %, preferably 5-50 wt %, more preferably 10-40 wt %.

In the particulate composition of the present invention, an oil component (A) containing reduced coenzyme $Q_{10}$ is polydispersed, forming preferably not less than 5 domains, more preferably not less than 1,000, more preferably not less than 10,000, particularly preferably not less than 100,000 in the matrix containing a water-soluble excipient. While the upper limit is not particularly limited, it is generally about 1,000,000,000.

When the number of domain in the matrix containing a water-soluble excipient is less than 5, the content of reduced coenzyme $Q_{10}$ in the finally-obtained particulate composition decreases, which unpreferably requires ingestion of a large amount of particulate composition for the oral administration of a given amount of reduced coenzyme $Q_{10}$.

In the present invention, the particulate composition preferably shows a sphericity of not less than 0.8, more preferably not less than 0.85, most preferably not less than 0.9. When the sphericity of the particulate composition is high, the total surface area per unit weight of the particulate composition becomes small. As a result, the particulate composition is not easily subject to an oxidation reaction due to the oxygen molecules in the air assumed to proceed from the particle surface. On the other hand, when the sphericity of a particulate composition is low, the total surface area per unit weight of the particulate composition becomes high. As a result, the particulate composition is easily subject to an oxidation reaction due to the oxygen molecules in the air assumed to proceed from the particle surface, and a particulate composition having high oxidative stability, which is one of the objects of the present invention, tends to be difficult to obtain. In other words, the present inventors have found that even when reduced coenzyme $Q_{10}$ having the same composition is contained in particulate compositions, the oxidative stability of the reduced coenzyme $Q_{10}$ having high oxidative stability in the particulate compositions varies depending on the sphericity thereof.

The sphericity of a particulate composition can be determined by photographing a target particulate composition with an electron microscope etc., and from a diameter ratio of the diameter of a circle having the same area and a smallest circumscribing circle, using an image analysis software Win-ROOF Ver.3.30 and the like.

Moreover, in the particulate composition of the present invention, when the particle size is approximately the same, a composition having a smaller surface roughness (Ra) is more preferable. It is considered that the smaller the surface roughness (Ra) of a particulate composition is, the smaller becomes the total surface area per unit weight of the particulate composition, and the particulate composition is not easily subject to an oxidation reaction due to the oxygen molecules in the air assumed to proceed from the particle surface. In contrast, when the surface roughness (Ra) of a particulate composition is large, the total surface area per unit weight of the particulate composition becomes large. As a result, the particulate composition is easily subject to an oxidation reaction due to the oxygen molecules in the air assumed to proceed from the particle surface, and a particulate composition having high oxidative stability, which is one of the objects of the present invention, tends to be difficult to obtain.

The surface roughness (Ra) of a particle can be determined, for example, as arithmetic average surface roughness (Ra) defined in JIS B 0601-1994. The surface roughness here is considered to be in an opposite relationship with the above-mentioned sphericity, where the sphericity is high, the surface roughness tends to be small.

In the particulate composition of the present invention, not less than 10 wt % of reduced coenzyme $Q_{10}$ in the composition is generally non-crystalline, i.e., amorphous or molten. Preferably not less than 20 wt %, more preferably not less than 50 wt %, more preferably not less than 70 wt %, particularly preferably not less than 80 wt %, and 100 wt % at maximum is not crystalline. In general, when preserved at not higher than the melting point, reduced coenzyme Q gradually shifts to a crystalline state. In the particulate composition obtained by the below-mentioned preferable production method, for example, not less than 10 wt % of the reduced coenzyme $Q_{10}$ in the composition is not crystalline even after preservation at 25° C. in the air for 30 days after production. Reduced coenzyme $Q_{10}$ is maintained in an amorphous or molten state in the particulate composition, rather than a crystalline state. Thus, reduced coenzyme $Q_{10}$ in an oil component (A), which is released upon disintegration of the particulate composition by gastric juice or intestinal juice after oral administration, is assumed to maintain an amorphous or molten state. In general, reduced coenzyme $Q_{10}$ in an amorphous or molten state is more susceptible to emulsification in the stomach or intestine by surfactant ingredients co-existing in the living body or particulate composition, rather than reduced coenzyme $Q_{10}$ in a crystalline state. As a result, absorption of reduced coenzyme $Q_{10}$ in an amorphous or molten state from the gastrointestinal tract is more easily promoted than reduced coenzyme $Q_{10}$ in a crystalline state. Consequently, the preferable particulate composition of the present invention is considered to acquire high oral absorbability, which is one of the objects thereof. In the particulate composition of the present invention, its structure is controlled to allow an oil component (A) containing reduced coenzyme $Q_{10}$ to be a polydispersion by forming a domain in the water-soluble excipient matrix. In a preferable production method, for example, since a molten oil component (A) containing reduced coenzyme $Q_{10}$ is enclosed in a microcapsule surrounded by a water-soluble excipient, the probability of development of the crystal nucleus of reduced coenzyme $Q_{10}$ drastically decreases, and the amorphous or molten state of particles is maintained for a long time after its formation. In other words, the structure of the particulate composition of the present invention, wherein an oil component (A) containing reduced coenzyme $Q_{10}$ (A) is polydispersed forming a domain in a matrix containing a water-soluble excipient, is assumed to be extremely important for realizing high oral absorbability.

While the volume average particle size of the particulate composition of the present invention is not particularly limited as long as the object of the present invention can be achieved. In view of the easiness of recovery as a powder and the like, it is preferably not less than 1 µm, more preferably not less than 5 µm, more preferably not less than 10 µm, particularly preferably not less than 20 µm, especially preferably not less than 50 µm. The upper limit of the volume average particle size is not particularly limited as long as the high stability and high absorbability of reduced coenzyme $Q_{10}$, which is the object of the present invention, can be maintained. For easy processing into food, pharmaceutical product, cosmetic and the like, it is preferably not more than 5000 µm, more preferably not more than 2000 µm, more preferably not more than 1000 µm, particularly preferably not more than 800 µm, especially preferably not more than 700 µm. That is, the volume average particle size of the particulate composition of the present invention is preferably 1-5000 µm, more preferably 5-2000 μm, still more preferably 10-1000 μm, particularly preferably 20-800 μm, especially preferably 50-700 μm. The volume average particle size can be measured using, for example, an ethanol solvent in a laser diffraction scattering type particle size distribution measurement apparatus (Microtruck MT3000II manufactured by NIKKISO CO., LTD.).

In addition, the particulate composition of the present invention can contain various additives and active ingredients other than coenzyme $Q_{10}$ usable for various objects in respective uses of food, cosmetics and pharmaceutical products according to each object.

For example, in addition to the above-mentioned compounds, excipients such as crystalline cellulose, calcium phosphate, calcium sulfate and the like, disintegrants such as calcium citrate, calcium carbonate, sodium hydrogencarbonate, dextrin, crystalline cellulose, carboxymethylcellulose, tragacanth, alginic acid and the like, lubricants such as talc, magnesium stearate, polyethylene glycol, silica, hydrogenated oil and the like, pigments such as titanium oxide, foodcolor, colcothar, safflower pigment, caramel pigment, gardenia pigment, tar pigment, chlorophyll and the like, antiblocking agents such as stearic acid, talc, light anhydrous silicic acid, hydrated silicon dioxide and the like, absorption promoters such as higher alcohols, higher fatty acids and the like, solubilizing agents such as fumaric acid, succinic acid, malic acid and the like, stabilizers such as benzoic acid, sodium benzoate, ethyl p-oxybenzoate, bees wax and the like can be used.

The active ingredient other than coenzyme $Q_{10}$ is not particularly limited as long as it is acceptable to be used for food, cosmetic or pharmaceutical product and, for example, glutathione, L-cysteine, N-acetylcysteine, alpha-lipoic acid, tocotrienol, vitamin E (α-tocopherol) and ester derivative thereof, erythorbic acid and ester derivative and salt thereof, vitamin A and ester derivative thereof, carotenoid, zeaxanthine, astaxanthin, lycopene, flavonoid, L-carnitine and pharmacologically acceptable salt thereof such as tartrate and fumarate thereof and the like, acetyl-L-carnitine, propionyl-L-carnitine, magnesium, zinc, selenium, manganese, riboflavin, niacinamide, curcuminoid, proanthocyanidin extracted from grape seed and pine bark, NADH (reduced nicotinamideadenine dinucleotide), NADPH (reduced nicotinamideadenine dinucleotide phosphate), resveratrol, bilberryan extract, milk thistle extract, highly unsaturated fatty acid obtained by concentration from fish oil and the like, ester derivative of vitamin C and the like can be mentioned. Preferably, glutathione, L-cysteine, tocotrienol, vitamin E (α-tocopherol) and ester derivative thereof, erythorbic acid and ester derivative and salt thereof, vitamin A and ester derivative thereof, carotenoid, rutin, astaxanthin, lycopene, flavonoid and L-carnitine can be mentioned. Of these, antioxidants such as carotenoid, astaxanthin, vitamin E and ester derivative thereof and the like are preferable from the aspect of stability of reduced coenzyme $Q_{10}$. Needless to say, various components recited here can also be used as a mixture of two or more kinds thereof.

Now the production method of the particulate composition containing reduced coenzyme $Q_{10}$ of the present invention is explained. The particulate composition of the present invention is preferably obtained by the following production method. However, if a similar particulate composition can be obtained by a different production method, the production method is not limited to the following.

The particulate composition containing reduced coenzyme $Q_{10}$ of the present invention can be preferably produced by (1) a method comprising suspending a oil-in-water emulsion composition prepared from an oil component (A) containing reduced coenzyme $Q_{10}$ and an aqueous solution containing a water-soluble excipient in oil component (B), and removing water from the oil-in-water emulsion composition in oil component (B) (hereinafter referred to as production method (1)), or, (2) a method comprising spray-drying, in a gaseous phase, a oil-in-water emulsion composition prepared from an oil component (A) containing reduced coenzyme $Q_{10}$ and an aqueous solution containing a water-soluble excipient (hereinafter referred to as production method (2)).

In the above-mentioned production methods (1) and (2), the water-soluble excipient is preferably used in the form of an aqueous solution dissolved in water, where the concentration is free of any particular limitation. It is preferable to handle at a concentration at which the viscosity of aqueous solution does not exceed 1 Poise, since the transferring property and the like can be ensured. Specific examples and preferable examples of the water-soluble excipient here are the same as those recited in the above-mentioned explanation of the particulate composition.

In the above-mentioned production methods (1) and (2), a most convenient and preferable preparation method of the oil component (A) containing reduced coenzyme $Q_{10}$ includes, but is not limited to, adding, where necessary, fat and oil and/or surfactant (D) and the like to reduced coenzyme $Q_{10}$ melted at not less than 50° C., and mixing by stirring and the like. Specific examples and preferable examples of oil component (A) here are the same as those recited in the above-mentioned explanation of the particulate composition.

In the production methods (1) and (2) of the present invention, the oil-in-water emulsion composition is prepared from the above-mentioned oil component (A) containing reduced coenzyme $Q_{10}$, and an aqueous solution containing a water-soluble excipient. In the above-mentioned preparation method of the oil-in-water emulsion composition, for example, it is most convenient and preferable to add an oil component (A) containing reduced coenzyme $Q_{10}$ prepared at a temperature not less than the melting point of reduced coenzyme $Q_{10}$ to an aqueous solution containing a water-soluble excipient, which was heated in advance to not less than 50° C., and finely disperse or emulsify oil component (A) to a desired average particle size using a known emulsification apparatus such as high-pressure homogenizer etc. In addition, it is possible to add a reduced coenzyme $Q_{10}$ powder, together with, where necessary, other oil component to an aqueous solution containing a water-soluble excipient, which was heated in advance to not less than 50° C., melt reduced coenzyme $Q_{10}$ with/without other oil component in an aqueous solution of water-soluble excipient, and emulsify the mixture, or directly add reduced coenzyme $Q_{10}$ powder or as a melt at not less than 50° C. and, where necessary, other oil component to an aqueous solution containing a water-soluble excipient, heat the mixture to not less than 50° C. to melt reduced coenzyme $Q_{10}$ and other oil component and emulsify the mixture. However, the method is not limited to these.

In the production method of the present invention, the emulsion particle size of an oil component (A) containing reduced coenzyme $Q_{10}$ of the above-mentioned oil-in-water emulsion composition is not particularly limited. When the average particle size of oil component (A) in the oil-in-water emulsion composition is large, the absorbability of the particulate composition may decrease. Thus, it is generally not more than 50 μm, preferably not more than 20 μm, more preferably not more than 15 μm, particularly preferably not more than 10 μm. When the average particle size of oil component (A) in the oil-in-water emulsion composition is small, problems occur in that excess water-soluble excipient is needed to maintain stability of emulsion droplet during the production process, excess load is applied to an emulsification apparatus and the like. Thus, the average particle size is generally 0.001 μm, preferably not less than 0.05 μm, more preferably not less than 0.1 μm. By controlling the particle size of the emulsion droplet in this step, the domain particle size of the obtained particulate composition can be controlled.

The above-mentioned emulsion particle size of oil component (A) in the oil-in-water emulsion composition can be measured using a commercially available laser diffraction • scattering type particle size distribution measurement apparatus.

In the production methods (1) and (2) of the present invention, the temperature of the step for preparing a oil-in-water emulsion composition from an oil component (A) containing reduced coenzyme $Q_{10}$ and an aqueous solution containing a water-soluble excipient and emulsion step is not particularly limited as long as it is not less than the temperature at which reduced coenzyme $Q_{10}$ in the oil-in-water composition is melted. Generally, it is not less than 50° C., preferably not less than 55° C., more preferably not less than 60° C. The upper limit is the boiling point of the system, which varies depending on the conditions such as pressurization and the like and the temperature cannot be defined generally. In the case of normal pressure conditions, the temperature is generally not more than 100° C., preferably not more than 90° C.

In the production method (1) of the present invention, the above-mentioned oil-in-water emulsion composition is mixed with a different oil component (B), and the oil-in-water emulsion composition is suspended in oil component (B) to a desired particle size, whereby an O/W/O emulsion can be produced. The above-mentioned mixing operation is, for example, most conveniently and preferably performed by adding a oil-in-water emulsion composition containing reduced coenzyme $Q_{10}$ to oil component (B) heated in advance to not less than 50° C. However, the method is not limited to this. The size of the particles suspended in the oil-in-water emulsion composition in oil component (B) can be adjusted by stirring, circulation of solution etc., or applying shear to the mixture. The temperature of oil component (B) during preparation of the mixture is preferably generally within the range of 50-100° C. to prevent rapid evaporation of water.

While the mixing ratio of the oil-in-water emulsion composition and oil component (B) in the production method (1) of the present invention is free of any particular limitation, the weight percentage of the oil-in-water emulsion composition in the mixture of the oil-in-water emulsion composition and oil component (B) is preferably not less than 1 wt %, more preferably not less than 10 wt %, particularly preferably not less than 15 wt %, from the aspect of production efficiency and the like. In addition, it is preferably not more than 70 wt %, particularly preferably not more than 60 wt %, particularly preferably not more than 50 wt %, from the aspect of suspendability in oil component (B) of the oil-in-water emulsion composition and the like. It is generally 1-70 wt %, preferably 10-60 wt %, particularly preferably 15-50 wt %.

In the production method (1) of the present invention, the above-mentioned O/W/O emulsion is afforded and then water is removed from the oil-in-water emulsion composition suspended in oil component (B). For removal of water from the oil-in-water emulsion composition, for example, the composition is heated to not less than 80° C., preferably not less than 100° C., under atmospheric pressure to evaporate water. Alternatively, a method including setting the temperature to a temperature not less than the boiling point of water (at the corresponding pressure), under any reduced pressure, and evaporating water and the like can be mentioned, but the method is not limited thereto. From the aspects of shortening of operation time and the like, the removal is preferably performed under any reduced pressure.

In the present invention, oil component (B) in production method (1) is a component containing fat and oil or, where necessary, surfactant (E). The fats and oils to be used for oil component (B) are not particularly limited as long as they can suspend the above-mentioned oil-in-water emulsion composition and may be, for example, natural fats and oils from plants and animals, or synthetic fats and oils or processed fats and oils. More preferably, they are acceptable for food, cosmetic or pharmaceutical agent. Examples of the vegetable oil include coconut oil, palm oil, palm kernel oil, flaxseed oil, camellia oil, brown rice germ oil, canola oil, rice oil, peanuts oil, corn oil, wheat germ oil, soy bean oil, perilla oil, cottonseed oil, sunflower kerel oil, kapok oil, evening primrose oil, shea butter, sal butter, cacao butter, sesame oil, safflower oil olive oil, and the like, and examples of animal fats and oils include lard, milk fat, fish oil, beef fat and the like. Furthermore, fats and oils obtained by processing them by fractionation, hydrogenation, transesterification (e.g., hydrogenated oil) and the like are also included. It is needless to say that medium-chain triglyceride (MCT) can also be used. In addition, a mixture thereof may be used.

Examples of the medium-chain triglyceride include triglyceride wherein fatty acid has 6 to 12 carbon atoms, preferably 8 to 12 carbon atoms Of the above-mentioned fats and oils, vegetable fats and oils, synthetic fats and oils and processed fats and oils are preferable from the aspects of handlability, odor and the like. For example, coconut oil, palm oil, palm kernel oil, canola oil, rice oil, soy bean oil, cottonseed oil, safflower oil, olive oil, MCT and the like can be used.

In production method (1) of the present invention, oil component (B) may be fat and oil alone. Where necessary, oil component (B) can contain surfactant (E). The droplet of the oil-in-water emulsion composition gradually comes to have greater adhesiveness as the progress of drying, and particles tend to easily agglomerate with each other. However, in the co-presence of surfactant (E) in oil component (B), agglomeration of oil-in-water emulsion composition droplets with increased adhesiveness during drying is drastically reduced and, as a result, the recovery rate of particulate composition having a desired volume average particle size can preferably be improved strikingly.

While the content of surfactant (E) in oil component (B) is free of any particular limitation, the wt % of surfactant (E) relative to oil component (B) is generally not less than 0.001 wt %, preferably not less than 0.005 wt %, more preferably not less than 0.01 wt %, from the aspect of suppression of agglomeration during drying of the oil-in-water emulsion composition droplets and the like. While the upper limit is not particularly limited, it is generally not more than 95 wt %, preferably not more than 80 wt %, more preferably not more than 60 wt %, from the aspect of flowability of oil component (B), removal of surfactant (E) and the like.

The above-mentioned surfactant (E) is not particularly limited as long as it is acceptable to be used for food, cosmetic or pharmaceutical product. A surfactant acceptable for food is particularly preferable and, for example, surfactants such as glycerol fatty acid esters, polyglycerol esters, sucrose fatty acid esters, sorbitan fatty acid esters, polyoxyethylenesorbitan fatty acid ester and the like, and lecithins, which have an HLB of not more than 10, can be used. Needless to say, they may be used alone or in a mixture of two or more kinds thereof in the present invention.

Examples of glycerol fatty acid esters include monoglycerides and diglycerides wherein fatty acid has 6 to 18, preferably 12 to 18, carbon atoms.

Examples of polyglycerol esters include polyglycerol fatty acid esters obtained by esterification of one or more hydroxyl groups of polyglycerin comprising polyglycerin having a polymerization degree of 2 to 10 as a main component with fatty acid(s) having 6 to 18, preferably 12 to 18, carbon atoms, polyglycerin condensed ricinoleic acid esters and the like.

Examples of sucrose fatty acid esters include one wherein one or more hydroxyl groups of sucrose is/are esterified with fatty acid having 6 to 18, preferably 12 to 18, carbon atoms.

Examples of sorbitan fatty acid esters include one wherein one or more hydroxyl groups of sorbitan is/are esterified with fatty acid having 6 to 18, preferably 12 to 18, carbon atoms.

Examples of the polyoxyethylenesorbitan fatty acid esters include one wherein one or more hydroxyl groups of sorbitan has/have a polyoxyethylene chain and one or more hydroxyl groups is/are esterified with fatty acid having 6 to 18, preferably 6 to 12, carbon atoms.

Examples of lecithins include egg-yolk lecithin, purified soybean lecithin, phosphatidylcholine, phosphatidylethanolamine, phosphatidylserine, sphingomyelin, dicetyl phosphate, stearylamine, phosphatidylglycerol, phosphatidic acid, phosphatidylinositolamine, cardiolipin, ceramide phosphorylethanolamine, ceramide phosphoryl glycerol, enzymatically decomposed lecithin (lysolecithin) and a mixture thereof and the like.

HLB of the above-mentioned surfactant (E) is preferably not more than 10, more preferably not more than 7, most preferably not more than 5 because agglomeration of oil-in-water emulsion composition droplets during drying can be efficiently suppressed. Lecithins can be preferably used without any limitation of HLB.

Specific example of such surfactant is a mixture of one or more kinds selected from monoglycerol monofatty acid esters such as monoglycerol monostearate, monoglycerol monooleate, monoglycerol monomyristate, monoglycerol monocaprylate, monoglycerol monolaurate, monoglycerol monobehenate, monoglycerol monoerucate and the like; monoglycerol difatty acid esters such as monoglycerol distearate, monoglycerol dioleate, monoglycerol dicaprylate, monoglycerol dilaurate and the like; fatty acid and organic acid esters of monoglycerol such as stearic acid and citric acid ester of monoglycerol, stearic acid and acetic acid ester of monoglycerol, hydrogenated coconut oil and acetic acid ester of monoglycerol, stearic acid and succinic acid ester of monoglycerol, caprylic acid and succinic acid ester of monoglycerol, stearic acid and lactic acid ester of monoglycerol, stearic acid and diacetyltartaric acid ester of monoglycerol and the like; monoglycerol fatty acid esters obtained using various fats and oils such as hydrogenated beef tallow and fatty acid esters of monoglycerol, hydrogenated canola oil and fatty acid esters of monoglycerol, hydrogenated soybean oil and fatty acid esters of monoglycerol, cottonseed oil and fatty acid esters of monoglycerol, safflower oil and fatty acid esters of monoglycerol and the like; polyglycerol esters such as polyglycerol fatty acid esters (e.g., an ester of polyglycerin having an average degree of polymerization of 2-10 and a fatty acid having 6 to 22 carbon atoms and the like), and polyglycerin condensed ricinoleate (e.g., an ester of polyglycerin having an average degree of polymerization of 2-10 and polyricinoleic acid having a condensation degree of 2-4 and the like) and the like; propylene glycol fatty acid esters such as propylene glycol monostearate, propylene glycol monooleate, propylene glycol monolaurate and the like; sorbitan fatty acid esters such as sorbitan distearate, sorbitan tristearate, sorbitan sesquioleate, sorbitan dioleate, sorbitan trioleate and the like; polyoxyethylenesorbitan fatty acid ester such as polyoxyethylenesorbitan monostearate, polyoxyethylenesorbitan monooleate and the like; lecithins such as soybean lecithin, egg-yolk lecithin, enzymatically decomposed lecithin and the like. Of the above-mentioned, a mixture of one or more kinds selected from glycerol fatty acid esters, polyglycerol fatty acid esters, polyglycerin condensed ricinoleates and lecithins is preferable, a mixture of one or more kinds selected from monoglycerol monofatty acid esters, monoglycerol difatty acid esters, fatty acid and organic acid esters of monoglycerol (particularly fatty acid and acetic acid esters of monoglycerol, hydrogenated coconut oil and acetic acid ester of monoglycerol), polyglycerol fatty acid esters (particularly an ester of polyglycerin having an average degree of polymerization of 2-10 and a fatty acid having 6 to 22 carbon atoms) and polyglycerin condensed ricinoleates (particularly an ester of polyglycerin having an average degree of polymerization of 2-10 and polyricinoleic acid having a condensation degree of 2-4) is more preferable, and fatty acid and organic acid esters of monoglycerol (particularly fatty acid and acetic acid esters of monoglycerol, hydrogenated coconut oil and acetic acid ester of monoglycerol, specifically 50% acetylated product of monoglycerol monostearate, completely acetylated product of hydrogenated coconut oil monoglyceride), tetraglycerol pentaoleate, polyglycerin condensed ricinoleate, egg-yolk lecithin, soybean lecithin, enzymatically decomposed lecithin are still more preferable.

In the production method (1) of the present invention, use of MCT as fat and oil and egg-yolk lecithin, soybean lecithin or enzymatically decomposed lecithin as surfactant (E) in combination is particularly preferable.

In the production method (1) of the present invention, the time necessary for removing water from oil-in-water emulsion composition droplets is free of any particular limitation. It is preferably within the range of 5 sec-24 hr, more preferably 1 min-12 hr, most preferably 5 min-6 hr. The time necessary for removing water of less than 5 sec is not preferable because violent bubbling occurs due to instantaneous evaporation of water from oil component (B). On the other hand, the time necessary for removing water of longer than 24 hr is not preferable because producibility is degraded.

Even if water is not completely removed, removal of water in the production method (1) of the present invention is sufficient as long as drying of oil-in-water emulsion composition droplets proceeds and recovery as particles is possible. The residual water content is generally preferably not more than 30 wt %, more preferably not more than 10 wt %, most preferably not more than 5 wt %, of the weight of recovered particles.

In the above-mentioned production method (1), the method of recovering the particulate composition after removal of water is not particularly limited. It is most convenient and preferable to remove oil component (B) by solid-liquid separation, wash the obtained particulate composition with an organic solvent etc. to wash away most part of oil component (B), evaporate the organic solvent and recover the composition as a powder.

The organic solvent used for washing oil component (B) is not particularly limited as long as it can dissolve and remove oil component (B). It is preferably an organic solvent usable for the production of food, pharmaceutical product, cosmetic and the like.

Examples of the solvent include ethanol, methanol, isopropanol, acetone, hexane, ethyl acetate, tetrahydrofuran and the like. Of these, ethanol is most preferable when the particulate composition of the present invention is used for food. The above-mentioned organic solvent can be dried by, but is not limited to, vacuum drying, drying by heating, air drying and the like. The particulate composition after recovery may be subjected to a classification operation to have a desirable particle size of a given product.

In the production method (2) of the present invention, as mentioned above, the particulate composition of the present invention can be obtained by spray drying, in a gaseous phase, a oil-in-water emulsion composition prepared from an oil component (A) containing reduced coenzyme $Q_{10}$ and an aqueous solution containing a water-soluble excipient. For spray drying in a gaseous phase, what is called a spray dry method can be used. The conditions for spray drying can be appropriately selected from the conditions generally employed.

Of the above-mentioned two kinds of production methods, production method (1) is a more preferable production method since a particulate composition having high oxidative stability, high sphericity and small surface roughness (Ra), which is the object of the present invention, tends to be easily obtained because removal of water proceeds while individual oil-in-water emulsion composition droplets suspended in a nearly spherical shape in oil component (B) maintain the spherical shape.

A particulate composition containing reduced coenzyme $Q_{10}$ having a nearly spherical shape and small surface roughness (Ra) can also be formed by production method (2) by appropriately controlling the temperature and residence time and the like during drying.

The stabilizing method and handling method of the particulate composition containing reduced coenzyme $Q_{10}$ of the present invention are now explained.

The stabilization as referred to in the present specification means suppression of oxidation of reduced coenzyme $Q_{10}$ to oxidized coenzyme $Q_{10}$. The handling as referred to in the present specification means maintaining or exerting the function of a certain object by applying an external action on the object. While examples of handling is not limited, they include taking out from a coating machine, wrapping, packaging, preservation, storage, transport and classification, with preference given to preservation.

The upper limit of the temperature of the stabilizing method and handling method of the particulate composition containing reduced coenzyme $Q_{10}$ of the present invention is generally not more than about 100° C., preferably not more than about 80° C., more preferably not more than about 60° C., more preferably not more than about 40° C., particularly preferably not more than about 20° C. In this case, the lower limit of the temperature is generally not less than about −100° C., preferably not less than about −80° C., more preferably not less than about −60° C., more preferably not less than about −40° C., particularly preferably not less than about −20° C.

The reduced coenzyme $Q_{10}$ residual ratio (%) after preservation at 40° C. in the air for 30 days under shading conditions of the particulate composition containing reduced coenzyme $Q_{10}$ of the present invention is not particularly limited. It is not less than about 50 wt %, preferably not less than about 60 wt %, more preferably not less than about 70 wt %, still more preferably not less than about 80 wt %, particularly preferably not less than about 90 wt %.

The present invention provides a stabilizing method and a handling method of a particulate composition containing reduced coenzyme $Q_{10}$ and a preparation containing the composition, which are characterized by controlling the relative humidity. In the stabilizing method or handling method of the present invention, the humidity of the preservation atmosphere is important. By controlling the humidity, the stability of the particulate composition containing reduced coenzyme $Q_{10}$ can be markedly improved. The upper limit of the relative humidity is not particularly limited as long as a particulate composition containing reduced coenzyme $Q_{10}$ can be preserved stably. Generally, a particulate composition containing reduced coenzyme $Q_{10}$ can be more stably handled under an environment adjusted to the relative humidity of not more than about 90%, preferably not more than about 80%, more preferably not more than about 70%, particularly preferably not more than about 60%. The lower limit of the relative humidity is 0%.

The above-mentioned environment with adjusted relative humidity can be afforded by dehumidification of the environment or introduction of a dehumidificated gas (e.g., air, preferably dry inert gas such as dry nitrogen and the like) into the environment and the like. While the above-mentioned dehumidification is not particularly limited, it is achieved by moisture freezing, use of a dehumidification machine, desiccant agent (silica gel, calcium chloride, synthesis zeolite etc.) and the like. Needless to say, the method is not particularly questioned as long as the environment with adjusted relative humidity can be afforded.

To maximally exert the effect of the invention and from the aspect of the stability of reduced coenzyme $Q_{10}$, the production and preservation of the particulate composition of the present invention is naturally preferably performed under a deoxygenation atmosphere. For example, it is preferably performed under a deoxygenation atmosphere using an inert gas such as nitrogen gas, argon gas etc., and the like.

The present invention provides a stabilizing method and a handling method of a particulate composition containing reduced coenzyme $Q_{10}$, which is obtained in the present invention, which is characterized by wrapping or packaging with a glass, plastic and/or metal material. The stability of the particulate composition is markedly improved by wrapping or packaging with the above-mentioned material.

As the glass material, for example, soft glass, hard glass and the like can be used. As the plastic material, for example, high density polyethylene, medium density polyethylene, low density polyethylene, polypropylene, polyethylene terephthalate, polyvinyl alcohol, polyvinyl chloride, polyvinylidene chloride, nylon and the like can be used. Needless to say, a film laminated with the above-mentioned plastic material, a film laminated with aluminum and the like on a plastic material such as aluminum laminate and the like, and a film obtained by vapor depositing aluminum, alumina, silica and the like on a plastic material are also included in the plastic materials.

As the metal material, for example, iron, aluminum, zinc, nickel, cobalt, copper, tin, titanium, chrome or alloy thereof (stainless, brass etc.) can be used. In addition, an enameled material using glass and metal in combination and the like can also be used.

The above-mentioned materials are preferably formed into a bottle, bag, can, drum, box and the like and used for wrapping or packaging the particulate composition of the present invention. Using the above-mentioned materials, moreover, PTP packaging, three-sided seal packaging, four-sided seal packaging, pillow packaging, strip packaging, aluminum molded packaging, stick packaging and the like can also be performed. When a material having comparatively low gas barrier and moisture-proof properties such as polyethylene and the like is used, double wrapping or packing or more is preferable. In this case, use of a material having comparatively high gas barrier and moisture-proof properties such as aluminum laminate, vapor deposition films (e.g., aluminum, alumina, silica and the like), glass, metal and the like is particularly preferable. After wrapping and packing, the composition can be transported or preserved in, where necessary, iron steel drum, resin drum, fiber drum, corrugated board and the like.

In the present invention, the above-mentioned stabilizing method or handling method of a particulate composition containing reduced coenzyme $Q_{10}$, which uses a moisture-proof agent in combination, is provided. Using a moisture-proof agent in combination, the stability of the particulate composition is markedly improved. As the moisture-proof agent, silica gel, calcium chloride, synthesis zeolite and the like can be used.

The residual ratio of reduced coenzyme $Q_{10}$ after preservation at 40° C. in the air for 30 days under shading conditions in the aforementioned environment in a preservation atmosphere where the humidity has been adjusted, and/or in a wrapping or packing form is not particularly limited. It is generally not less than about 80 wt %, preferably not less than about 85 wt %, more preferably not less than about 90 wt %, still more preferably not less than about 95 wt %, particularly preferably not less than about 97 wt %. Needless to say, it is possible to afford an environment where the humidity has been adjusted by employing the above-mentioned wrapping or packaging form.

The particulate composition containing reduced coenzyme $Q_{10}$, which is obtained in the present invention, can be processed into or used as a pharmaceutical agent, food, cosmetic and the like in the form of a preparation such as tablet, pill, capsule (hard capsule, soft capsule, microcapsule and the like), chewable tablet, powder preparation, granule, syrup, drinkable preparation and the like, and the like. That is, the preparation in this context does not refer solely to a pharmaceutical agent but also encompasses the aforementioned form belonging to food and cosmetics. For preparation making, excipient, disintegrant, lubricant, binder, anticoagulant, absorption promoter, dissolving agent, stabilizer and the like can be used. For forming a capsule, fat and oil, surfactants such as lecithin, lysolecithin and the like can also be used in combination.

From the aspect of the stability of a particulate composition containing reduced coenzyme $Q_{10}$, in a preferable embodiment of the above-mentioned preparation, handling or preservation in the aforementioned environment where the humidity has been adjusted and/or the aforementioned wrapping or packaging for handling or preservation is employed.

The present invention further provides reduced coenzyme $Q_{10}$ in a non-crystalline state at a temperature not more than the melting temperature, and further, reduced coenzyme $Q_{10}$ wherein at least a part of the reduced coenzyme $Q_{10}$ is in a non-crystalline state. Generally, the present invention provides reduced coenzyme $Q_{10}$ wherein not less than 10 wt %, preferably not less than 20 wt %, more preferably not less than 50 wt %, more preferably not less than 70 wt %, particularly preferable not less than 80 wt %, 100 wt % at maximum, is in a non-crystalline state. As used herein, the non-crystalline state means an amorphous state or molten state.

The reduced coenzyme $Q_{10}$ in a non-crystalline state can be produced by the production method of the aforementioned particulate composition because the reduced coenzyme $Q_{10}$ contained in oil component (A) of particulate composition obtained by this method is generally in a non-crystalline state.

As other production method, for example, a method including bringing a first aerosol fluid containing a water-soluble polymer solution having the properties to form a physical gel and reduced coenzyme $Q_{10}$ and a second aerosol fluid containing a gelling agent into contact with each other can be employed.

Here, the "water-soluble polymer solution having the property to form a physical gel" is a water-soluble polymer capable of forming a gel-like crosslinked state by hydrogen bond and ion bond between polymers, chelate formation and the like. The "property to form a physical gel" means a property affording a visually observable change from viscous fluid (sol) to an elastic form (gel) by the addition of inorganic salt or acid, or application of an operation such as heating, cooling and the like to an aqueous solution of a water-soluble polymer.

Examples of the above-mentioned water-soluble polymer include water-soluble alginic acid and derivative thereof, low methoxylpectin, gelatin, xanthan gum, carmellose sodium, polyvinylpyrrolidone, water-soluble cellulose and derivative thereof and the like.

Examples of the gelling agent include an aqueous solution of calcium chloride, magnesium chloride or barium chloride and the like.

As a method for contacting a water-soluble polymer solution containing reduced coenzyme $Q_{10}$ with a coagulation agent (gelling agent), for example, a given amount of an aqueous solution of a coagulation agent (gelling agent) is continuously sprayed in an aerosol state to form a coagulating gaseous phase atmosphere, a water-soluble polymer solution containing reduced coenzyme $Q_{10}$ preferably in an emulsion state is continuously sprayed or added dropwise in the atmosphere.

In this way, reduced coenzyme $Q_{10}$-containing granules can be obtained. The reduced coenzyme $Q_{10}$ contained in the granules generally contains at least a non-crystalline state.

EXAMPLES

The present invention is explained in more detail in the following by referring to Examples, which are not to be construed as limitative.

(Purity of Reduced Coenzyme $Q_{10}$)

The purity of reduced coenzyme $Q_{10}$ and the weight ratio (%) of reduced coenzyme $Q_{10}$ were determined by the following HPLC analysis (weight ratio (%)={reduced coenzyme $Q_{10}$/(oxidized coenzyme $Q_{10}$+reduced coenzyme $Q_{10}$)}×100).

The HPLC analysis conditions are described below.
column: SYMMETRY C18 (manufactured by Waters) 250 mm (length) 4.6 mm (inner diameter),
mobile phase; $C_2H_5OH/CH_3OH=4/3$ (v/v),
detection wavelength; 210 nm,
flow rate; 1.0 ml/min,
retention time of reduced coenzyme $Q_{10}$; 9.1 min,
retention time of oxidized coenzyme $Q_{10}$; 13.3 min.

(Sphericity)

The sphericity of the obtained particulate composition was determined by analyzing, using an image analysis software (WinROOF Ver.3.30), the images obtained by observation of the recovered particles with an electron microscope and from a diameter ratio of the diameter of a circle having the same area and a smallest circumscribing circle. For the analysis, 20 samples were analyzed and the average value was determined.

(Crystallinity)

The crystallinity of reduced coenzyme $Q_{10}$ in the obtained particulate composition was determined by the following DSC (differential scanning calorimeter [EXSTAR6000 manufactured by Seiko Instruments Inc.]) analysis after preservation at 25° C. in the air for 30 days. The particulate compositions obtained in Examples and Comparative Examples were preserved under the above-mentioned given conditions, 10 mg thereof was taken in an aluminum pan and the temperature was elevated from 15° C. to 70° C. at a temperature rise rate of 5° C./min, during which the crystal melting calorie was measured. The crystallinity was calculated according to the following formula using the theoretical melting calorie determined from the content of reduced coenzyme $Q_{10}$ in the particulate composition and the data of melting calorie actually measured by DSC.

Crystallinity (%)=(measured melting calorie/theoretical melting calorie)×100

(Volume Average Particle Size)

The volume average particle size of the obtained particulate composition was measured by a laser diffraction scattering type particle size distribution measurement apparatus (Microtruck MT3000II manufactured by NIKKISO CO., LTD.) using an ethanol solvent.

(Domain Average Particle Size)

The obtained particulate composition was added to a two-component curable adhesive (Araldite handled by As One Co. Ltd.) and cured. The obtained embedded sample was immersed in liquid nitrogen for 5 min, sufficiently cooled and ruptured using a hammer. The broken-out section was immersed in hexane for 15 min to remove oil component (A), and the broken-out section of the particulate composition was photographed with a scanning electron microscope (S-4800; Hitachi). The average particle size of the domain was determined by selecting any 50 voids from randomly taken images, measuring the particle size thereof and taking the average thereof.

Production Example

Oxidized coenzyme $Q_{10}$ crystal (100 g, manufactured by Kaneka Corporation) and L-ascorbic acid (60 g) were added to ethanol (1000 g) and the mixture was stirred at 78° C. to carry out a reduction reaction. After 30 hr, the mixture was cooled to 50° C., and ethanol (400 g) and water (100 g) were added while maintaining the same temperature. With stirring, the ethanol solution was cooled to 2° C. at a cooling rate of 10° C./hr, washed with cold ethanol and cold water in this order, and the obtained wet crystals were dried under reduced pressure to give white dry crystals (95 g) (yield 95 mol %). All the operations except drying under reduced pressure were performed under a nitrogen atmosphere. The purity of the obtained crystals was 99.1% and the weight ratio (%) of the reduced coenzyme $Q_{10}$ relative to the total amount of coenzyme Q was 99.0%.

Example 1

Gum arabic (60 g, gum arabic A manufactured by Ina Food Industry Co., Ltd.) was dissolved in distilled water (332 g) at 30° C. to give an aqueous water-soluble excipient solution. After heating the aqueous solution to 60° C., reduced coenzyme $Q_{10}$ powder (8 g) obtained in the above-mentioned Production Example was added and melted, and then the solution was emulsified by TK homomixer MarkII (manufactured by PRIMIX Corporation) at 10000 rpm×5 min to give an oil-in-water emulsion composition. The emulsion particle size (average particle size of domain) of the reduced coenzyme $Q_{10}$ in the oil-in-water emulsion composition was about 1 μm. The oil-in-water emulsion composition was spray dried with a hot air using a spray dryer (B-290 manufactured by Nihon BUCHI K.K.) under the condition of the hot air inlet temperature of 200° C. to give a particulate composition containing reduced coenzyme $Q_{10}$.

The obtained particulate composition had sphericity; 0.87, volume average particle size; 6.9 μm, coenzyme Q content; 11.8 wt % and reduced coenzyme Q content; 11.1 wt %. FIG. 1 shows an electron micrograph of the appearance of the obtained particulate composition. The residual ratio of the reduced coenzyme $Q_{10}$ after preservation at 40° C. in the air in light shading for 30 days was 83%. In addition, the crystallinity measured by DSC was 21%.

Example 2

Gelatin (30 g, APH-250 manufactured by Nitta Gelatin Inc.) was dissolved in distilled water (336 g) at 60° C. to give an aqueous water-soluble excipient solution. The aqueous solution was maintained at 60° C., reduced coenzyme $Q_{10}$ powder (4 g) obtained in the above-mentioned Production Example was added and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 0.5 μm. The oil-in-water emulsion composition was spray dried with a hot air using a spray dryer (B-290 manufactured by Nihon BUCHI K.K.) under the condition of the hot air inlet temperature of 200° C. to give a particulate composition containing reduced coenzyme $Q_{10}$.

The obtained particulate composition had sphericity; 0.83, coenzyme Q content; 11.8 wt % and reduced coenzyme Q content; 10.8 wt %. The residual ratio of the reduced coenzyme $Q_{10}$ after preservation at 40° C. in the air in light shading for 30 days was 63%. In addition, the crystallinity measured by DSC was 27%.

Example 3

Soybean polysaccharides (40 g, S-ZR100 manufactured by FUJI OIL CO., LTD.) were dissolved in distilled water (360 g) at 60° C. to give an aqueous water-soluble excipient solution. The aqueous solution was maintained at 60° C., reduced coenzyme $Q_{10}$ powder (6.2 g) obtained in the above-mentioned Production Example was added and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition was spray dried with a hot air using a spray dryer (B-290 manufactured by Nihon BUCHI K.K.) under the condition of the hot air inlet temperature of 200° C. to give a particulate composition containing reduced coenzyme $Q_{10}$.

The obtained particulate composition had sphericity; 0.81, coenzyme Q content; 13.4 wt % and reduced coenzyme Q content; 12.5 wt %. The residual ratio of the reduced coenzyme $Q_{10}$ after preservation at 40° C. in the air in light shading for 30 days was 79%. In addition, the crystallinity measured by DSC was 36%.

Example 4

Gelatin (18 g, APH-250 manufactured by Nitta Gelatin Inc.) was dissolved in distilled water (182 g) at 60° C., and an aqueous yeast cell wall solution (200 g, YeastWrap manufactured by Kirin Brewery Co., LTD.) was added thereto to give an aqueous water-soluble excipient solution. The aqueous solution was maintained at 60° C., reduced coenzyme $Q_{10}$ powder (5.4 g) obtained in the above-mentioned Production Example was added and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition was spray dried with a hot air using a spray dryer (B-290 manufactured by Nihon BUCHI K.K.) under the condition of the hot air inlet temperature of 200° C. to give a particulate composition containing reduced coenzyme $Q_{10}$.

The obtained particulate composition had sphericity; 0.84, coenzyme Q content; 13.2 wt % and reduced coenzyme Q content; 12.2 wt %. The residual ratio of the reduced coenzyme $Q_{10}$ after preservation at 40° C. in the air in light shading for 30 days was 64%. In addition, the crystallinity measured by DSC was 49%.

Example 5

Gum arabic (60 g, gum arabic A manufactured by Ina Food Industry Co., Ltd.) was dissolved in distilled water (140 g) at 30° C. to give an aqueous water-soluble excipient solution. The aqueous solution was heated to 60° C., reduced coenzyme $Q_{10}$ powder (9.2 g) obtained in the above-mentioned Production Example was added and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (145 g, Actor M-2 manufactured by Riken Vitamin Co., Ltd.) and a surfactant (5 g, polyglycerin condensed ricinolate: SY Glyster CRS-75 manufactured by Sakamoto Yakuhin Kogyo Co., Ltd.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.97, volume average particle size; 130 μm, domain particle size; 1.4 μm, coenzyme Q content; 12.8 wt % and reduced coenzyme Q content; 11.9 wt %. The residual ratio of the reduced coenzyme $Q_{10}$ after preservation at 40° C. in the air in light shading for 30 days was 100%. In addition, the crystallinity measured by DSC was 0%.

Figure 2:
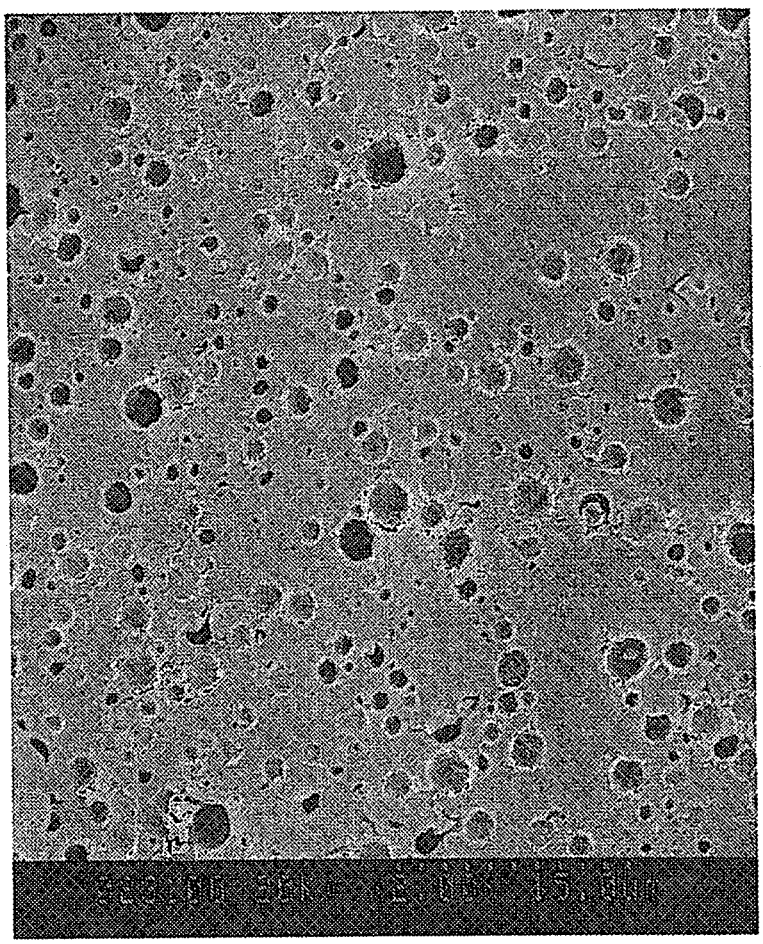
FIG. 2 shows an electron micrograph of the section of the particulate composition obtained in Example 5.

The electron micrograph of the section of the obtained particulate composition is shown in FIG. 2. As shown in FIG. 2, it was confirmed that the domains formed by oil component (A) were polydispersed as ultrafine voids in the particulate composition. From this picture, the number of domains in one particle is assumed to be about 100,000.

Example 6

Gum arabic (60 g, gum arabic A manufactured by Ina Food Industry Co., Ltd.) was dissolved in distilled water (140 g) at 30° C. to give an aqueous water-soluble excipient solution. Separately, oil component (A) obtained by uniformly mixing reduced coenzyme $Q_{10}$ powder (9.2 g) obtained in the above-mentioned Production Example and a surfactant (4.2 g, diglycerol monooleate: poem DO-100V manufactured by Riken Vitamin Co., Ltd.) at 60° C. was added to an aqueous water-soluble excipient solution at 60° C., and then the mixture was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 0.5 μm. The oil-in-water emulsion composition (75 g) obtained here was added to oil component (B) consisting of MCT (145 g, Actor M-2 manufactured by Riken Vitamin Co., Ltd.) and a surfactant (5 g, polyglycerin condensed ricinolate: SY Glyster CRS-75 manufactured by Sakamoto Yakuhin Kogyo Co., Ltd.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The sphericity of the obtained particulate composition was 0.97, and coenzyme Q content was 11.6 wt % and reduced coenzyme Q content was 10.7 wt %. The residual ratio of the reduced coenzyme $Q_{10}$ after preservation at 40° C. in the air in light shading for 30 days was 100%. In addition, the crystallinity measured by DSC was 0%.

Example 7

Gelatin (40 g, APH-250 manufactured by Nitta Gelatin Inc.) was dissolved in distilled water (160 g) at 60° C. to give an aqueous water-soluble excipient solution. The aqueous solution was heated to 60° C., reduced coenzyme $Q_{10}$ powder (6.2 g) obtained in the above-mentioned Production Example was added and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 0.5 μm. The oil-in-water emulsion composition (75 g) obtained here was added to oil component (B) consisting of MCT (145 g, Actor M-2 manufactured by Riken Vitamin Co., Ltd.) and a surfactant (5 g, polyglycerin condensed ricinolate: SY Glyster CRS-75 manufactured by Sakamoto Yakuhin Kogyo Co., Ltd.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.97, volume average particle size; 131 μm, coenzyme Q content; 12.3 wt % and reduced coenzyme Q content; 11.3 wt %. The residual ratio of the reduced coenzyme $Q_{10}$ after preservation at 40° C. in the air in light shading for 30 days was 94%. In addition, the crystallinity measured by DSC was 0%.

Figure 3:
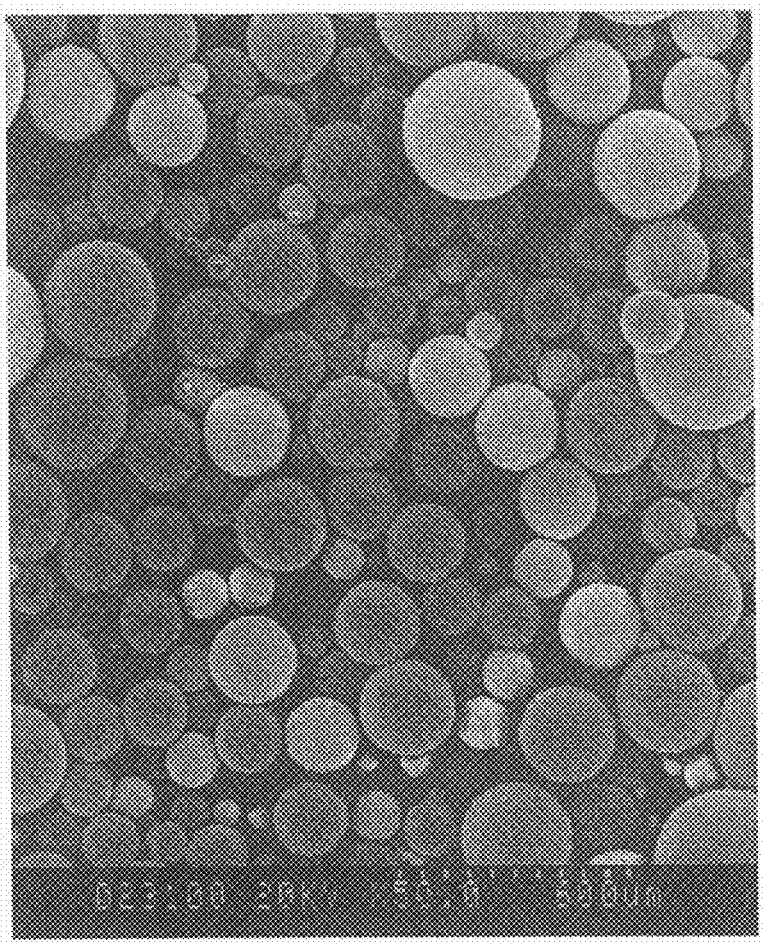
FIG. 3 shows an electron micrograph of the appearance of the particulate composition obtained in Example 7.

The electron micrograph of the appearance of the obtained particulate composition is shown in FIG. 3. As shown in FIG. 3, it was confirmed that the particulate composition obtained in Example 7 had high sphericity.

Example 8

Gum arabic (60 g, gum arabic A manufactured by Ina Food Industry Co., Ltd.) was dissolved in distilled water (140 g) at 30° C. to give an aqueous water-soluble excipient solution. The aqueous solution was heated to 60° C., reduced coenzyme $Q_{10}$ powder (25.7 g) obtained in the above-mentioned Production Example was added and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1.5 μm. The oil-in-water emulsion composition (75 g) obtained here was added to oil component (B) consisting of MCT (145 g, Actor M-2 manufactured by Riken Vitamin Co., Ltd.) and a surfactant (5 g, polyglycerin condensed ricinolate: SY Glyster CRS-75 manufactured by Sakamoto Yakuhin Kogyo Co., Ltd.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.97, domain particle size; 1.4 μm, coenzyme Q content; 30 wt % and reduced coenzyme Q content; 29.5 wt %. The residual ratio of the reduced coenzyme $Q_{10}$ after preservation at 40° C. in the air in light shading for 30 days was 100%. In addition, the crystallinity measured by DSC was 0%.

Figure 4:
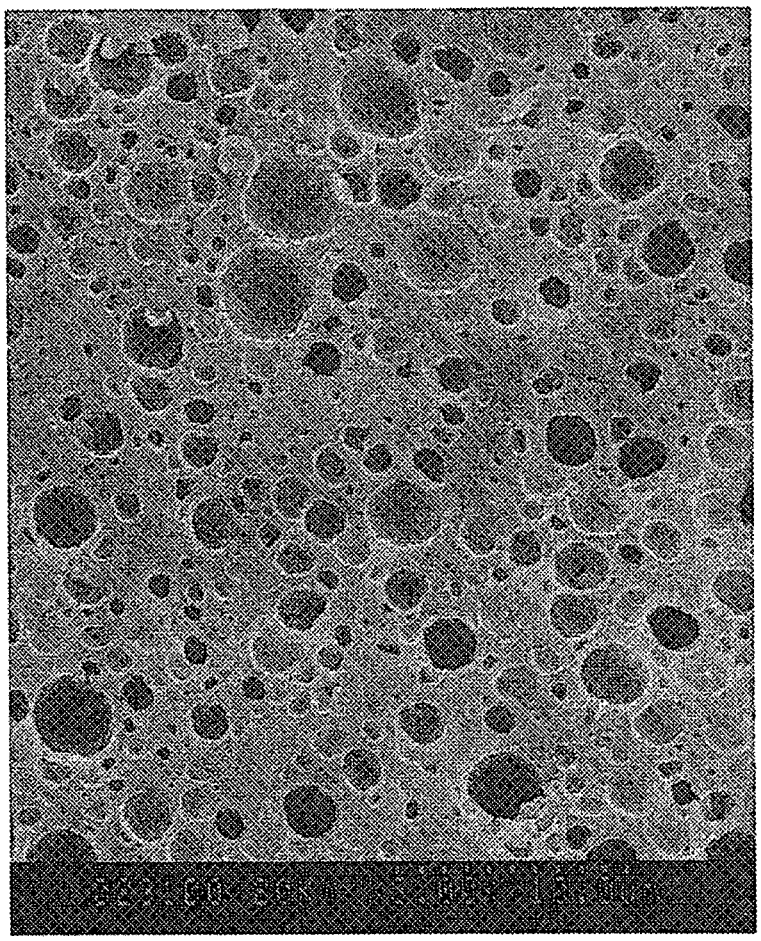
FIG. 4 shows an electron micrograph of the section of the particulate composition obtained in Example 8.

The electron micrograph of the section of the obtained particulate composition is shown in FIG. 4. As shown in FIG. 4, it was confirmed that the domains formed by oil component (A) were polydispersed as ultrafine voids in the particulate composition. From this picture, the number of domains in one particle is assumed to be about 250,000.

Example 9

Gum arabic (60 g, gum arabic A manufactured by Ina Food Industry Co., Ltd.) was dissolved in distilled water (140 g) at 30° C. to give an aqueous water-soluble excipient solution. The aqueous solution was heated to 60° C., reduced coenzyme $Q_{10}$ powder (9.2 g) obtained in the above-mentioned Production Example was added and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (100 g, Actor M-2 manufactured by Riken Vitamin Co., Ltd.) and a surfactant (50 g, tetraglycerol pentaoleate: SY Glyster PO-3S, HLB3.0 manufactured by Sakamoto Yakuhin Kogyo Co., Ltd.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.97, coenzyme Q content; 12.3 wt % and reduced coenzyme Q content; 11.6 wt %.

The residual ratio of the reduced coenzyme $Q_{10}$ after preservation at 40° C. in the air in light shading for 30 days was 99%. In addition, the crystallinity measured by DSC was 0%.

Example 10

Gum arabic (45 g, gum arabic A manufactured by Ina Food Industry Co., Ltd.) and gelatin (15 g, APH-250 manufactured by Nitta Gelatin Inc.) were dissolved in distilled water (140 g) at 60° C. to give an aqueous water-soluble excipient solution. Separately, oil component (A) obtained by uniformly mixing reduced coenzyme $Q_{10}$ powder (9.2 g) obtained in the above-mentioned Production Example and a surfactant (4.2 g, diglycerol monooleate: poem DO-100V manufactured by Riken Vitamin Co., Ltd.) at 60° C. was added to an aqueous water-soluble excipient solution at 60° C., and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (75 g, Actor M-2 manufactured by Riken Vitamin Co., Ltd.) and a surfactant (75 g, tetraglycerol pentaoleate: SY Glyster PO-3S, HLB3.0 manufactured by Sakamoto Yakuhin Kogyo Co., Ltd.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.96, coenzyme Q content; 12.5 wt % and reduced coenzyme Q content; 11.5 wt %. The residual ratio of the reduced coenzyme $Q_{10}$ after preservation at 40° C. in the air in light shading for 30 days was 97%. In addition, the crystallinity measured by DSC was 0%.

Example 11

Gum arabic (30 g, gum arabic A manufactured by Ina Food Industry Co., Ltd.) gelatin (10 g, APH-250 manufactured by Nitta Gelatin Inc.), sucrose (17.5 g, manufactured by Wako Pure Chemical Industries, Ltd.) and lactose (2.5 g, manufactured by Wako Pure Chemical Industries, Ltd.) were dissolved in distilled water (140 g) at 60° C. to give an aqueous water-soluble excipient solution. Separately, oil component (A) obtained by uniformly mixing reduced coenzyme $Q_{10}$ powder (9.2 g) obtained in the above-mentioned Production Example and a surfactant (4.2 g, diglycerol monooleate: poem DO-100V manufactured by Riken Vitamin Co., Ltd.) at 60° C. was added to an aqueous water-soluble excipient solution at 60° C., and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (75 g, Actor M-2 manufactured by Riken Vitamin Co., Ltd.) and a surfactant (75 g, tetraglycerol pentaoleate: SY Glyster PO-3S, HLB3.0 manufactured by Sakamoto Yakuhin Kogyo Co., Ltd.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.87, coenzyme Q content; 12.5 wt % and reduced coenzyme Q content; 11.6 wt %. The residual ratio of the reduced coenzyme $Q_{10}$ after preservation at 40° C. in the air in light shading for 30 days was 97%. In addition, the crystallinity measured by DSC was 0%.

Example 12

Gum arabic (60 g, gum arabic A manufactured by Ina Food Industry Co., Ltd.) was dissolved in distilled water (140 g) at 30° C. to give an aqueous water-soluble excipient solution. Separately, reduced coenzyme $Q_{10}$ powder (9.2 g) obtained in the above-mentioned Production Example was added to an aqueous water-soluble excipient solution at 60° C. and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (149.6 g, Actor M-2 manufactured by Riken Vitamin Co., Ltd.) and an enzymatically decomposed lecithin (0.4 g, Emultop HL50 handled by Nihon SiberHegner K.K.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.97, coenzyme Q content; 13.3 wt % and reduced coenzyme Q content; 12.4 wt %. The residual ratio of the reduced coenzyme $Q_{10}$ after preservation at 40° C. in the air in light shading for 30 days was 99%. In addition, the crystallinity measured by DSC was 0%.

Example 13

Gum arabic (60 g, gum arabic A manufactured by Ina Food Industry Co., Ltd.) was dissolved in distilled water (140 g) at 30° C. to give an aqueous water-soluble excipient solution. Separately, reduced coenzyme $Q_{10}$ powder (9.2 g) obtained in the above-mentioned Production Example was added to an aqueous water-soluble excipient solution at 60° C. and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (148.5 g, Actor M-2 manufactured by Riken Vitamin Co., Ltd.) and lecithin (1.5 g, Emulpur IP handled by Nihon SiberHegner K.K.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.97, coenzyme Q content; 13.3 wt % and reduced coenzyme Q content; 12.4 wt %. The residual ratio of the reduced coenzyme $Q_{10}$ after preservation at 40° C. in the air in light shading for 30 days was 99%. In addition, the crystallinity measured by DSC was 0%.

Example 14

Gum arabic (60 g, gum arabic A manufactured by Ina Food Industry Co., Ltd.) was dissolved in distilled water (140 g) at 30° C. to give an aqueous water-soluble excipient solution. Separately, reduced coenzyme $Q_{10}$ powder (10.6 g) obtained in the above-mentioned Production Example and enzymatically decomposed lecithin (5.3 g, Emultop HL50 handled by Nihon SiberHegner K.K.) were added to an aqueous water-soluble excipient solution at 60° C. and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (150 g, Actor M-2 manufactured by Riken Vitamin Co., Ltd.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.97, coenzyme Q content; 13.9 wt % and reduced coenzyme Q content; 12.9 wt %. The residual ratio of the reduced coenzyme $Q_{10}$ after preservation at 40° C. in the air in light shading for 30 days was 99%. In addition, the crystallinity measured by DSC was 0%.

Example 15

Gum arabic (60 g, gum arabic A manufactured by Ina Food Industry Co., Ltd.) was dissolved in distilled water (140 g) at 30° C. to give an aqueous water-soluble excipient solution. Separately, reduced coenzyme $Q_{10}$ powder (10.6 g) obtained in the above-mentioned Production Example and lecithin (1.0 g, Iｪｼﾁﾝ-IP handled by Nihon SiberHegner K.K.) were added to an aqueous water-soluble excipient solution at 60° C. and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (150 g, Actor M-2 manufactured by Riken Vitamin Co., Ltd.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.97, coenzyme Q content; 13.3 wt % and reduced coenzyme Q content; 12.4 wt %. The residual ratio of the reduced coenzyme $Q_{10}$ after preservation at 40° C. in the air in light shading for 30 days was 99%. In addition, the crystallinity measured by DSC was 0%.

Example 16

Gum arabic (60 g, gum arabic A manufactured by Ina Food Industry Co., Ltd.), sucrose (20 g, manufactured by Wako Pure Chemical Industries, Ltd.) and lecithin (17.2 g, Iｪｼﾁﾝ-IP handled by Nihon SiberHegner K.K.) were dissolved in distilled water (140 g) at 30° C. to give an aqueous water-soluble excipient solution. Separately, reduced coenzyme $Q_{10}$ powder (17.2 g) obtained in the above-mentioned Production Example was added to an aqueous water-soluble excipient solution at 60° C. and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (149.6 g, Actor M-2 manufactured by Riken Vitamin Co., Ltd.) and an enzymatically decomposed lecithin (0.4 g, Emultop HL50 handled by Nihon SiberHegner K.K.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by adjusting the temperature of the suspension to 105° C. while continuing stirring at the aforementioned stirring number, and most of the water evaporated in about 30 min. Thereafter, oil component (B) was filtrated by solid-liquid separation according to a conventional method, and the oil component (B) attached to the particles was washed with ethanol (about 500 g) and dried at 50° C. to give a particulate composition containing reduced coenzyme $Q_{10}$.

The obtained particulate composition had sphericity; 0.97, volume average particle size; 309 μm, domain particle size; 0.6 μm, coenzyme Q content; 15 wt % and reduced coenzyme Q content; 14.0 wt %. The residual ratio of the reduced coenzyme $Q_{10}$ after preservation at 40° C. in the air in light shading for 30 days was 100%. In addition, the crystallinity measured by DSC was 0%.

Figure 5:
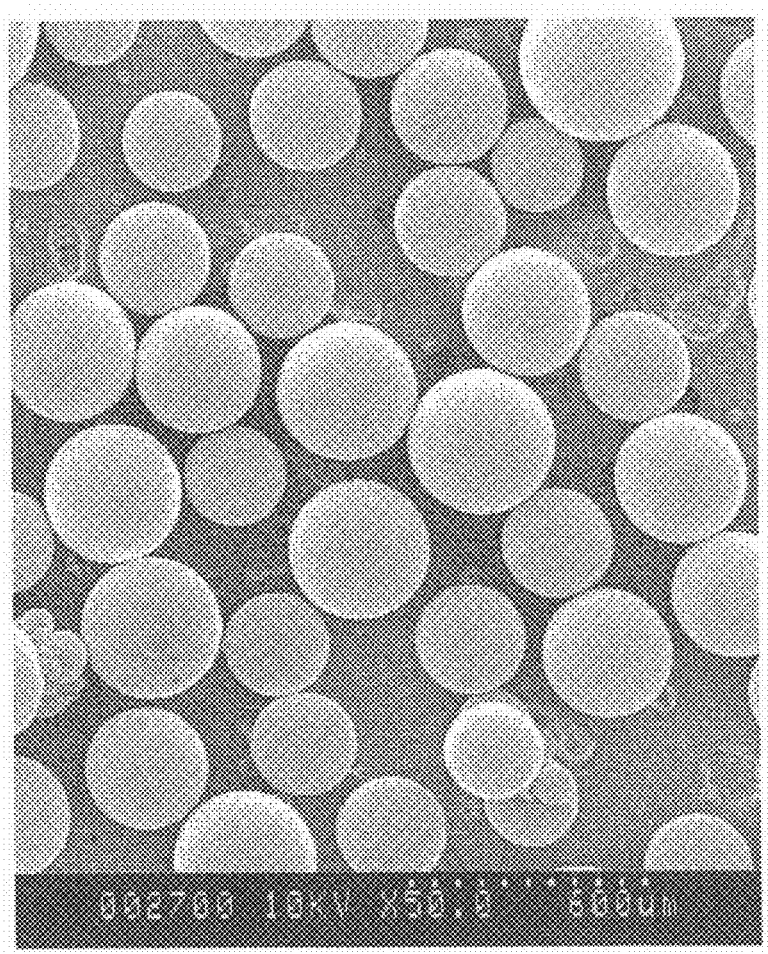
FIG. 5 shows an electron micrograph of the appearance of the particulate composition obtained in Example 16.
Figure 6:
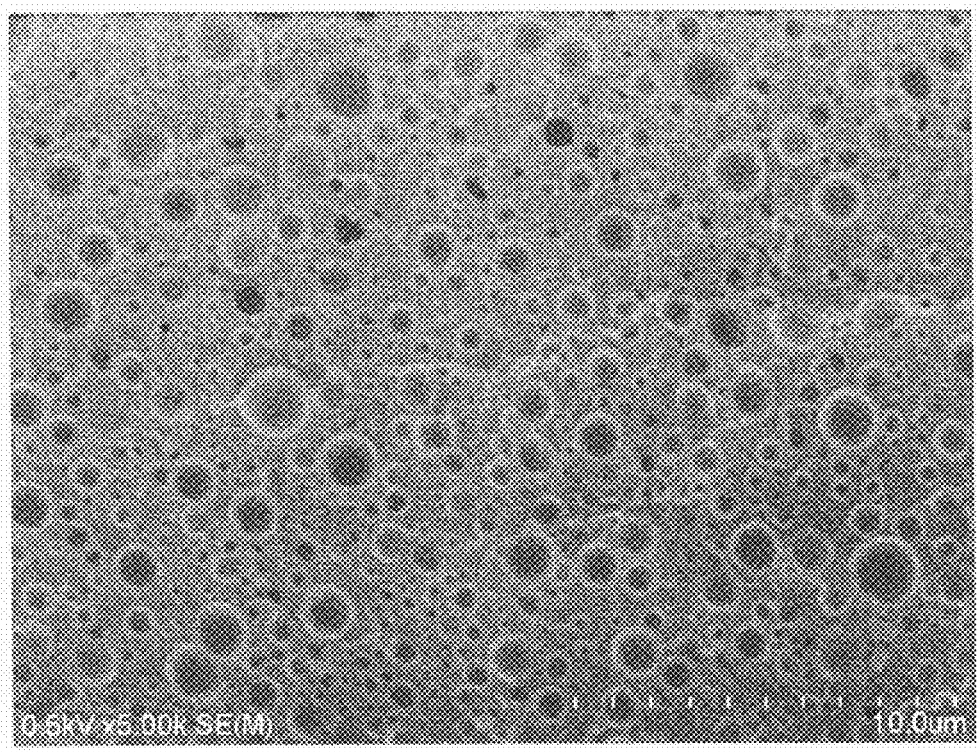
FIG. 6 shows an electron micrograph of the section of the particulate composition obtained in Example 16.

The electron micrographs of the appearance and section of the obtained particulate composition are shown in FIG. 5 and FIG. 6. As shown in FIG. 5, it was confirmed that the particulate composition obtained in Example 16 had high sphericity. As shown in FIG. 6, it was confirmed that the domains formed by oil component (A) were polydispersed as ultrafine voids in the particulate composition. From this picture, the number of domains in one particle is assumed to be about 20 million.

Comparative Example 1

White dry crystals of reduced coenzyme $Q_{10}$ obtained in Production Example were pulverized in a mortar to give a powder of reduced coenzyme $Q_{10}$.

The sphericity of the obtained powder was 0.78, and the residual ratio of the reduced coenzyme $Q_{10}$ after preservation at 40° C. in the air in light shading for 30 days was 28%. In addition, the crystallinity measured by DSC was 100%, and reduced coenzyme $Q_{10}$ in an amorphous or molten state was not contained.

From the Examples and Comparative Examples, it is clear that the particulate composition of the present invention has high sphericity, and the reduced coenzyme $Q_{10}$ contained in the particulate composition has improved oxidative stability.
(Evaluation of Oral Absorbability)

Male Slc:SD rats (9-week-old) (specified to be body weight 320 g or above on arrival) were used for the test. Five rats per group were preliminarily raised for 2 weeks. The rats were raised in an animal room set to room temperature 20-26° C., humidity 40-70%, lighting 12 hr/day (7:30-19:30), and allowed to freely take a solid feed CE-2 (manufactured by CLEA Japan, Inc.) and tap water. The body weight of the rats was measured one day before administration, and the amount of the sample to be filled in a capsule was calculated. Each sample was accurately measured to make the dose per body weight of rat 10 mg/kg body weight as the content of the reduced coenzyme $Q_{10}$, and filled in a gelatin hard capsule using an exclusive funnel.

The body weight of the rats was measured one day before the test, and the rats were grouped so that each group would have approximately the same average body weight.

For administration, a capsule administration machine (manufactured by TOAPAC) only for rat was used. Forsible oral administration to rat was performed using a hard capsule, the administration time was recorded on a given recording paper, and 1.5 ml/kg of distilled water was given immediately after the administration.

After administration to each group, blood samples (about 0.5 ml) were taken from the cervical vein at 1, 2, 4, 8 and 24 hr later. Then, the plasma was separated by a cooling centrifuge (4° C., 3000 rpm×20 min), and the obtained plasma was preserved in a freezer (−20° C.) until the analysis start date. The total plasma coenzyme $Q_{10}$ was quantified by HPLC according to a conventional method.

Figure 7:
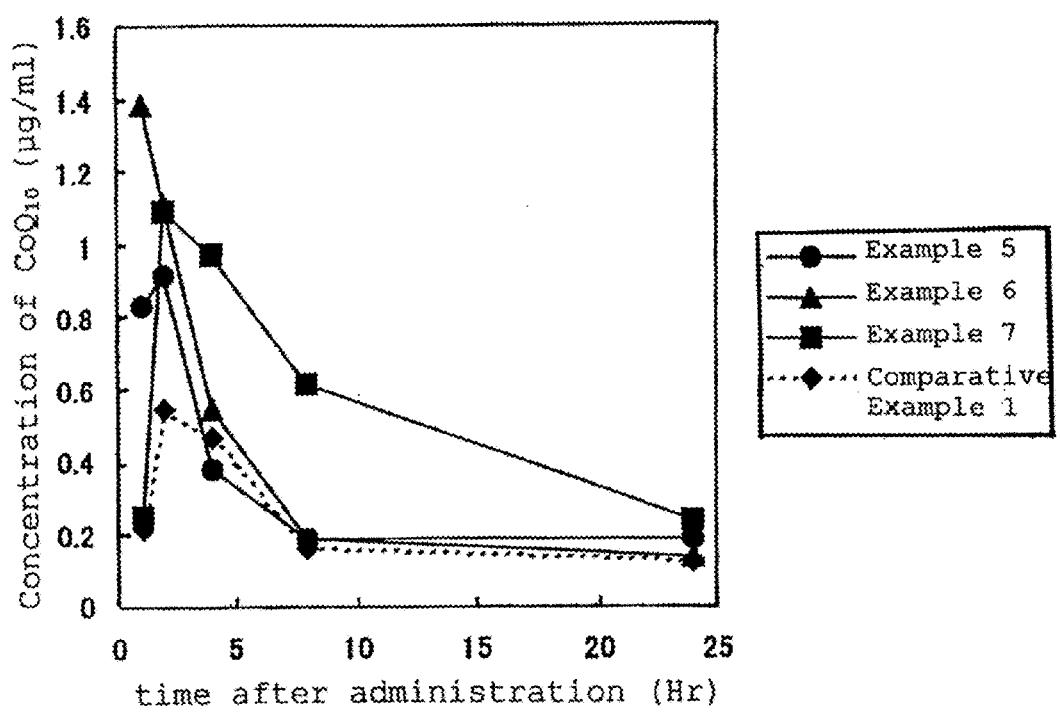
FIG. 7 shows test results of the oral absorbability of the particulate compositions obtained in Examples 5, 6 and 7, and the powder obtained in Comparative Example 1.

First, an oral absorbability test was performed by administering hard capsules directly filled with the particulate compositions obtained in the above-mentioned Examples 5, 6 and 7 or the powder obtained in Comparative Example 1. The results are shown in FIG. 7.

From the above-mentioned results, it can be confirmed that the oral absorbability of the reduced coenzyme $Q_{10}$ in the particulate composition of the present invention in an amorphous or molten state as evidenced by the crystallinity of 0% became extremely higher than conventional powder in a crystal state. That is, the particulate composition containing reduced coenzyme $Q_{10}$ of the present invention can be said to be a particulate composition simultaneously having high oxidative stability and high oral absorbability.

Figure 8:
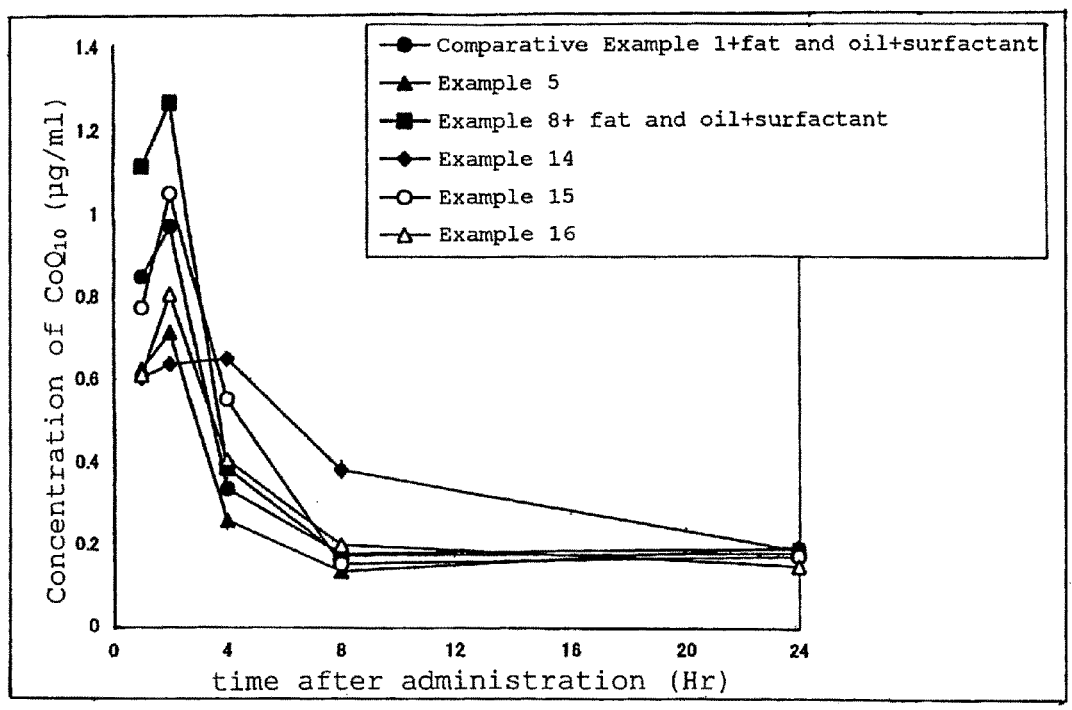
FIG. 8 shows test results of the oral absorbability when the particulate compositions obtained in Examples 5, 8, 14, 15 and 16 and the powder obtained in Comparative Example 1 were ingested.

Next, an oral absorbability test was performed by administering the particulate compositions obtained in Examples 5, 8, 14, 15 and 16 and the powder obtained in Comparative Example 1, and AUC was calculated. At this time, as for the particulate composition of the above-mentioned Example 8 and the powder of Comparative Example 1, the compositions prepared to have the following formulations were filled in hard capsules and the particulate compositions of the above-mentioned Examples 5, 14, 15 and 16 were directly filled in hard capsules. The results are shown in FIG. 8.

Hard capsule formulation of Example 8 (amount of use is each component amount per 1 kg of rat body weight): a mixture of the particulate composition obtained in Example 8 (33.3 mg, 10 mg as amount of reduced coenzyme $Q_{10}$), safflower oil (77.8 mg, oleic acid content of constituent fatty acid 76.6%), hexaglycerol monooleate (11.1 mg, SUNSOFT Q-17F manufactured by Taiyo Kagaku Co., Ltd.), enzymatically decomposed lecithin (11.1 mg, Emultop IP handled by Nihon SiberHegner K. K.).

Hard capsule formulation of Comparative Example 1 (amount of use is each component amount per 1 kg of rat body weight): a mixture of powder obtained in Comparative Example 1 (10 mg), canola oil (51.1 mg), diglycerol monooleate (21.9 mg, poem DO-100V manufactured by Riken Vitamin Co., Ltd.), bee wax (7.8 mg) and soybean lecithin (0.09 mg).

From the above-mentioned results, it is clear that particularly high oral absorbability is shown when lecithin is used as surfactant (D) or (E). In addition, it is clear that the oral absorbability is further improved even when lecithin is not used as surfactant (D) or (E), by taking the particulate composition of the present invention together with lecithin.

Preparation Example 1

"KANEKA QH (20 g, registered trademark)" (manufactured by Kaneka Corporation), which is reduced coenzyme $Q_{10}$, was melted by heating to 60° C., the melt was dispersed in an aqueous solution (1 L) containing sodium alginate (20 g, IL6-G manufactured by KIMICA Corporation) and adjusted to 60° C. in advance, and the mixture was emulsified using a homogenizer at 15000 rpm for 10 min to give an emulsion.

Preparation Example 2

"KANEKA QH (20 g, registered trademark)" (manufactured by Kaneka Corporation) was melted by heating to 60° C., the melt was dispersed in an aqueous solution (1 L) containing sodium alginate (20 g, IL6-G manufactured by KIMICA Corporation) and gelatin (50 g, APH Nitta Gelatin Inc.) and adjusted to 60° C. in advance, and the mixture was emulsified using a homogenizer at 15000 rpm for 10 min. The particle size (particle size distribution) of the emulsified particles containing coenzyme $Q_{10}$ in the uniform emulsion was measured with a dynamic light scattering particle size distribution measurement apparatus (LB-550 manufactured by Horiba, Ltd.) to find that the median particle size was 1 μm.

Preparation Example 3

In the same manner as in Preparation Example 1 except that decaglycerol monooleate (20 g, J-0381V manufactured by Riken Vitamin Co., Ltd.) and middle chain fatty acid triglycelite (10 g, Actor M-2 manufactured by Riken Vitamin Co., Ltd.) were added to the composition, an emulsion was obtained.

Example 17

Preparation of Particles Containing Reduced Coenzyme $Q_{10}$

The emulsions containing reduced coenzyme $Q_{10}$ obtained in Preparation Examples 1-3 were sprayed from the overhead of a cylindrical coagulation chamber having an inner diameter of 45 cm and the total height of about 5 m using a two-fluid nozzle (BIMJ2004 manufactured by H. IKEUCHI & Co., LTD.) as a spray means under the conditions of a volume average droplet diameter of 150 μm and a feed amount of 150 g/min. Simultaneously therewith, an aqueous calcium chloride solution having a concentration of 30 wt % was sprayed at a volume average droplet diameter of 1-10 μm using a two-fluid nozzle (1/4J series SU13A manufactured by Spraying Systems) while mixing with air so that the calcium chloride solid content would be 5-15 parts by weight relative to 100 parts by weight of the emulsion. To prevent the reduced coenzyme $Q_{10}$ emulsion sprayed from the overhead of the coagulation chamber from attaching to the wall of the coagulation chamber, distilled water at 25° C. was continuously supplied at 6 L/min into a pipe having an inner diameter of about 20 mm with many 2 mmφ pores formed in the side wall. The reduced coenzyme $Q_{10}$ containing emulsion was gelated while falling down in the coagulation chamber and became particles, and then recovered as a water suspension from the bottom. The recovered suspension was dehydrated and dried by a conventional method to give granules. Using an electron microscope, it was confirmed that particles having a volume average particle size of about 50 μm were prepared using any of the emulsions of Preparation Examples 1-3.

Example 18

Measurement of Crystallinity of Coenzyme $Q_{10}$ in Particles

The thermal analysis of the reduced coenzyme $Q_{10}$ granules obtained in Example 17 and the reduced coenzyme $Q_{10}$ powder "KANEKA QH (registered trademark)" (manufactured by Kaneka Corporation) used as a starting material in Preparation Examples 1-3 was performed under the following conditions using a differential scanning analytical calorimeter (EXSTAR6000 DSC6220 manufactured by SII). The results are shown in Table 1. The crystallinity was calculated from the measurement value of melting heat (ΔH).

Analysis conditions; 20° C.→80° C. (5° C./min)→−50° C. (−5° C./min)

TABLE 1

| sample | crystallinity |
|---|---|
| Example 17 (granule obtained from emulsion of Preparation Example 1) | 34% |
| Example 17 (granule obtained from emulsion of Preparation Example 2) | 34% |
| Example 17 (granule obtained from emulsion of Preparation Example 3) | 36% |

As a result, it was confirmed that the reduced coenzyme $Q_{10}$ particles of Example 17 contained non-crystalline reduced coenzyme $Q_{10}$.

Example 19

Gum arabic (75 g, gum arabic A manufactured by Ina Food Industry Co., Ltd.) and sucrose (25 g, manufactured by Wako Pure Chemical Industries, Ltd.) were dissolved in distilled water (140 g) at 30° C. to give an aqueous water-soluble excipient solution. Separately, reduced coenzyme $Q_{10}$ powder (45.0 g) obtained in the above-mentioned Production Example was added to an aqueous water-soluble excipient solution at 60° C. and melted, and then the solution was emulsified by TK homomixer MarkII (manufactured by PRIMIX Corporation) at 10000 rpm×5 min to give an oil-in-water emulsion composition. The emulsion particle size of the reduced coenzyme $Q_{10}$ in the oil-in-water emulsion composition was about 1 μm. The oil-in-water emulsion composition (75 g) obtained here was added to oil component (B) consisting of MCT (149.2 g, Actor M-2 manufactured by Riken Vitamin Co., Ltd.) and lecithin (0.8 g, Emulpur IP handled by Nihon SiberHegner K.K.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by continuing the stirring at the aforementioned stirring number and reducing the pressure while maintaining the inside temperature at not less than 70° C., and most of the water evaporated in about 20 min. Thereafter, oil component (B) was filtrated by solid-liquid separation according to a conventional method, and the oil component (B) attached to the particles was washed with ethanol (about 500 g). The obtained wet product was dried at about 40° C. to give 35 g of a particulate composition containing 30.2% of reduced coenzyme $Q_{10}$ (30.6% as coenzyme $Q_{10}$). The sphericity of the obtained particulate composition was 0.97. The residual ratio of the reduced coenzyme $Q_{10}$ after preservation of the obtained particulate composition at 40° C. in the air in light shading for 30 days was 99%. In addition, the crystallinity measured by DSC was 0%.

Example 20

The particulate composition (5 g) containing reduced coenzyme $Q_{10}$, which was obtained in Example 19, was placed in a polyethylene bag, and the polyethylene bag was placed in an aluminum laminated bag to package the particulate composition. The package was placed in a thermo-hygrostat tank at 40° C., relative humidity 80% and preserved in light shading for 30 days. The residual ratio of the reduced coenzyme $Q_{10}$ then was 100%.

Example 21

By packing in the same manner as in Example 20 except that 1 g of silica gel was placed in an aluminum laminated bag, a package of a particulate composition containing reduced coenzyme $Q_{10}$ was obtained. The package was placed in a thermo-hygrostat tank at 40° C., relative humidity 80% and preserved in light shading for 30 days. The residual ratio of the reduced coenzyme $Q_{10}$ then was 100%.

Example 22

The particulate composition (5 g) containing reduced coenzyme $Q_{10}$, which was obtained in Example 19, was placed in a polyethylene bag, and the polyethylene bag was placed in a polyethylene bag together with silica gel (3 g) to package the particulate composition. The package was placed in a thermo-hygrostat tank at 40° C., relative humidity 80% and preserved in light shading for 30 days. The residual ratio of the reduced coenzyme $Q_{10}$ then was 98%.

Example 23

The particulate composition (5 g) containing reduced coenzyme $Q_{10}$, which was obtained in Example 19, was placed in a glass bottle. The glass bottle was placed in a thermo-hygrostat tank at 40° C., relative humidity 80% and preserved in light shading for 30 days.

The residual ratio of the reduced coenzyme $Q_{10}$ then was 81%.

Example 24

Gum arabic (75 g, gum arabic A manufactured by Ina Food Industry Co., Ltd.) and dextrin (25 g, Pinedex #2, DE:11±1, manufactured by Matsutani Chemical Industry Co., Ltd.) were dissolved in distilled water (140 g) at 30° C. to give an aqueous water-soluble excipient solution. Separately, reduced coenzyme $Q_{10}$ powder (45.0 g) obtained in the above-mentioned Production Example was added to an aqueous water-soluble excipient solution at 60° C. and melted, and then the solution was emulsified by TK homomixer MarkII (manufactured by PRIMIX Corporation) at 10000 rpm×5 min to give an oil-in-water emulsion composition. The emulsion particle size of reduced coenzyme $Q_{10}$ in the oil-in-water emulsion composition was about 1 μm. The oil-in-water emulsion composition (75 g) obtained here was added to oil component (B) consisting of MCT (149.2 g, Actor M-2 manufactured by Riken Vitamin Co., Ltd.) and lecithin (0.8 g, Emulpur IP handled by Nihon SiberHegner K.K.), which was heated to 90° C. in advance, and the number of the stirring rotation was adjusted to set the particle size of the oil-in-water emulsion composition suspension droplet to about 200 μm. Removal of water from the oil-in-water emulsion composition suspension droplet proceeded by continuing the stirring at the aforementioned stirring number and reducing the pressure while maintaining the inside temperature at not less than 70° C., and most of the water evaporated in about 20 min. Thereafter, oil component (B) was filtrated by solid-liquid separation according to a conventional method, and the oil component (B) attached to the particles was washed with ethanol (about 500 g). The obtained wet product was dried at about 40° C. to give 35 g of a particulate composition containing 30.2% of reduced coenzyme $Q_{10}$ (30.7% as coenzyme $Q_{10}$).

The sphericity of the obtained particulate composition was 0.97. The residual ratio of the reduced coenzyme $Q_{10}$ after preservation of the obtained particulate composition at 40° C. in the air in light shading for 30 days was 99%.

Formulation Example 1

Soft Capsule

The particulate composition containing reduced coenzyme $Q_{10}$, which was obtained in Example 1, was added to a mixture of canola oil, diglycerol monooleate (poem DO-100V manufactured by Riken Vitamin Co., Ltd.), hydrogenated oil, bees wax and lecithin, and a gelatin soft capsule of the following formulation, which contained reduced coenzyme $Q_{10}$, was obtained by a conventional method.

| particulate composition containing | |
| --- | --- |
| reduced coenzyme $Q_{10}$ | 20.0 wt % |
| diglycerol monooleate | 12.0 wt % |
| canola oil | 53.0 wt % |
| hydrogenated oil | 7.0 wt % |
| bees wax | 6.0 wt % |
| lecithin | 2.0 wt % |

Formulation Example 2

Soft Capsule

The particulate composition containing reduced coenzyme $Q_{10}$, which was obtained in Example 19, was added to a mixture of canola oil, diglycerol monooleate (poem DO-100V manufactured by Riken Vitamin Co., Ltd.), hydrogenated oil, bees wax and lecithin, and a carageenan/starch soft capsule of the following formulation, which contained reduced coenzyme $Q_{10}$, was obtained by a conventional method.

| particulate composition containing | |
| --- | --- |
| reduced coenzyme $Q_{10}$ | 30.0 wt % |
| diglycerol monooleate | 12.0 wt % |
| canola oil | 43.0 wt % |
| hydrogenated oil | 8.0 wt % |
| bees wax | 5.0 wt % |
| lecithin | 2.0 wt % |

Formulation Example 3

Soft Capsule

The particulate composition containing reduced coenzyme $Q_{10}$, which was obtained in Example 14, was added to a mixture of canola oil, diglycerol monooleate (poem DO-100V manufactured by Riken Vitamin Co., Ltd.), hydrogenated oil and lecithin, and a gelatin soft capsule of the following formulation, which contained reduced coenzyme $Q_{10}$, was obtained by a conventional method.

| particulate composition containing | |
| --- | --- |
| reduced coenzyme $Q_{10}$ | 30.0 wt % |
| diglycerol monooleate | 12.0 wt % |
| canola oil | 40.0 wt % |
| hydrogenated oil | 16.0 wt % |
| lecithin | 2.0 wt % |

Formulation Example 4

Hard Capsule

The particulate composition containing reduced coenzyme $Q_{10}$, which was obtained in Example 19, was mixed with lactose. The obtained powder mixture was sized with a sieve, and a gelatin hard capsule of the following formulation, which contained reduced coenzyme $Q_{10}$, was obtained by a conventional method.

| particulate composition containing | |
| --- | --- |
| reduced coenzyme $Q_{10}$ | 60.0 wt % |
| lactose | 40.0 wt % |

Formulation Example 5

Chewable Tablet

The particulate composition containing reduced coenzyme $Q_{10}$, which was obtained in Example 19, was mixed with cornstarch and sucrose, and further mixed with magnesium stearate. The obtained powder mixture was sized with a sieve, the obtained sized powder was tabletted with a rotary tabletting machine to give a chewable tablet of the following formulation and containing a reduced coenzyme $Q_{10}$.

| particulate composition containing | |
| --- | --- |
| reduced coenzyme $Q_{10}$ | 47.0 wt % |
| cornstarch | 3.0 wt % |
| sucrose | 48.0 wt % |
| magnesium stearate | 2.0 wt % |

Formulation Example 6

Tablet

The particulate composition containing reduced coenzyme $Q_{10}$, which was obtained in Example 19, was mixed with crystalline cellulose (Avicel), and further mixed with magnesium stearate. The obtained powder mixture was sized with a sieve, the obtained sized powder was tabletted with a rotary tabletting machine to give a tablet of the following formulation and containing a reduced coenzyme $Q_{10}$.

| particulate composition containing | |
| --- | --- |
| reduced coenzyme $Q_{10}$ | 49.0 wt % |
| crystalline cellulose (Avicel) | 50.0 wt % |
| magnesium stearate | 1.0 wt % |

While some of the embodiments of the present invention have been described in detail in the above, those of ordinary skill in the art can enter various modifications and changes to the particular embodiments shown without substantially departing from the novel teaching and advantages of the present invention. Such modifications and changes are encompassed in the spirit and scope of the present invention as set forth in the appended claims.

This application is based on application Nos. 2006-172086 and 2007-114877 filed in Japan and U.S. provisional application No. 60/829,240, the contents of which are incorporated hereinto by reference.

The invention claimed is:

1. A particulate composition comprising an oil component (A), comprising reduced coenzyme $Q_{10}$, and a matrix comprising a water-soluble excipient, wherein the oil component (A) is polydispersed forming a domain in the matrix, and the particulate composition has a sphericity of not less than 0.9, a volume average particle size of 50-1000 μm; not less than 80 wt % of the reduced coenzyme $Q_{10}$ in the particulate composition is non-crystalline; and the obtained particulate composition has a residual ratio of the reduced coenzyme $Q_{10}$ of not less than 90 wt % after preservation at 40° in air in light shading for 30 days.

2. The particulate composition of claim 1, wherein the oil component (A) is polydispersed forming not less than 5 domains.

3. The particulate composition of claim 1, wherein the water-soluble excipient is at least one kind selected from the group consisting of a water-soluble polymer, a surfactant (C), sugar and a yeast cell wall.

4. The particulate composition of claim 3, wherein the water-soluble polymer is at least one kind selected from the group consisting of gum arabic, gelatin, agar, starch, pectin, carageenan, casein, dried albumen, curdlan, alginic acids, soybean polysaccharide, pullulan, celluloses, xanthan gum, carmellose salt and polyvinylpyrrolidone.

5. The particulate composition of claim 3, wherein the surfactant (C) is at least one kind selected from the group consisting of glycerol fatty acid ester, sucrose fatty acid ester, sorbitan fatty acid ester, polyoxyethylenesorbitan fatty acid ester, lecithins and saponins.

6. The particulate composition of claim 3, wherein the sugar is at least one kind selected from the group consisting of monosaccharide, disaccharide, oligosaccharide, sugar alcohol and polysaccharide.

7. The particulate composition of claim 1, wherein the oil component (A) containing reduced coenzyme $Q_{10}$ comprises 5-100 wt % of reduced coenzyme $Q_{10}$, 0-95 wt % of fat and oil, and 0-95 wt % of a surfactant (D).

8. The particulate composition of claim 7, wherein the surfactant (D) is at least one kind selected from the group consisting of glycerol fatty acid ester, polyglycerin ester, sucrose fatty acid ester, sorbitan fatty acid ester, propylene glycol fatty acid ester, and polyoxyethylenesorbitan fatty acid ester, each having an HLB of not more than 10, and lecithins.

9. The particulate composition of claim 1, wherein the content of the reduced coenzyme $Q_{10}$ in the particulate composition is 1-70 wt %.

10. The particulate composition of claim 1, wherein the domain formed by the oil component (A) has an average particle size of 0.01-50 μm.

11. A preparation comprising the particulate composition of claim 1.

12. A method of stabilizing a particulate composition or preparation comprising reduced coenzyme $Q_{10}$, which comprises placing the particulate composition of claim 1, in an environment of a surrounding relative humidity of not more than 90%.

13. A method of handling a particulate composition or preparation comprising reduced coenzyme $Q_{10}$, which comprises placing the particulate composition of claim 1, in an environment of a surrounding relative humidity of not more than 90%.

14. A method of stabilizing a particulate composition or preparation comprising reduced coenzyme $Q_{10}$, which comprises wrapping or packaging the particulate composition of claim 1 with a glass, plastic and/or metal material.

15. A method of handling a particulate composition or preparation comprising reduced coenzyme $Q_{10}$, which comprises wrapping or packaging the particulate composition of claim 1 with a glass, plastic and/or metal material.

16. The stabilizing method of claim 12, which comprises concurrently using a moisture-proof agent.

17. The handling method of claim 13, which comprises concurrently using a moisture-proof agent.

18. The particulate composition of claim 1, wherein the oil component (A) containing reduced coenzyme $Q_{10}$ comprises not less than 60 wt % of reduced coenzyme $Q_{10}$.

19. The particulate composition of claim 1, wherein the water-soluble excipient is a combination of water-soluble polymer and sugar.

20. The particulate composition of claim 3, wherein the water soluble polymer is at least one kind selected from the group consisting of gum arabic, gelatin and soybean polysaccharide.

* * * * *